US009758570B2

(12) United States Patent
Lim et al.

(10) Patent No.: US 9,758,570 B2
(45) Date of Patent: Sep. 12, 2017

(54) PREPARATION AND COMPOSITION OF INTER-ALPHA INHIBITOR PROTEINS FROM BLOOD

(71) Applicant: ProThera Biologics, Inc., Providence, RI (US)

(72) Inventors: Yow-Pin Lim, Providence, RI (US); Edward S. Sirya, New York, NY (US); Peter Brne, Ilirska Bistrica (SI)

(73) Assignee: ProThera Biologics, Inc., Providence, RI (US)

(*) Notice: Subject to any disclaimer, the term of this patent is extended or adjusted under 35 U.S.C. 154(b) by 0 days.

(21) Appl. No.: 14/859,705

(22) Filed: Sep. 21, 2015

(65) Prior Publication Data

US 2016/0145318 A1 May 26, 2016

Related U.S. Application Data

(62) Division of application No. 12/995,141, filed as application No. PCT/US2009/003291 on May 28, 2009, now Pat. No. 9,139,641.

(60) Provisional application No. 61/130,269, filed on May 28, 2008.

(51) Int. Cl.
*A61K 38/16* (2006.01)
*A61K 35/14* (2015.01)
*C07K 14/81* (2006.01)
*A61K 38/00* (2006.01)

(52) U.S. Cl.
CPC ............ *C07K 14/811* (2013.01); *A61K 38/00* (2013.01)

(58) Field of Classification Search
None
See application file for complete search history.

(56) References Cited

U.S. PATENT DOCUMENTS

| 4,839,298 | A | 6/1989 | Kay et al. |
| 5,166,133 | A | 11/1992 | Houston et al. |
| 5,777,081 | A | 7/1998 | Michalski et al. |
| 5,948,894 | A | 9/1999 | Berry et al. |
| 6,069,236 | A | 5/2000 | Burnouf-Radosevich et al. |
| 6,313,091 | B1 | 11/2001 | Wisniewski et al. |
| 6,489,128 | B1 | 12/2002 | Lim et al. |
| 6,660,482 | B1 | 12/2003 | Lim et al. |
| 6,673,908 | B1 | 1/2004 | Stanton, Jr. |
| 7,932,365 | B2 | 4/2011 | Lim et al. |
| 7,939,282 | B2 | 5/2011 | Fast et al. |
| 9,139,641 | B2 | 9/2015 | Lim et al. |
| 2003/0027848 | A1 | 2/2003 | Billotte et al. |
| 2003/0149062 | A1 | 8/2003 | Jung et al. |
| 2003/0190732 | A1 | 10/2003 | Josic |
| 2004/0009212 | A1 | 1/2004 | Tsai |
| 2006/0079670 | A1 | 4/2006 | Komatsoulis et al. |
| 2007/0160594 | A1 | 7/2007 | Filvaroff et al. |
| 2007/0172479 | A1 | 7/2007 | Warne et al. |
| 2007/0297982 | A1 | 12/2007 | Lim et al. |
| 2011/0190194 | A1 | 8/2011 | Lim et al. |
| 2011/0190208 | A1 | 8/2011 | kerstrom et al. |
| 2011/0236381 | A1 | 9/2011 | Garantziotis et al. |
| 2011/0293594 | A1 | 12/2011 | Teschner et al. |
| 2012/0028269 | A1 | 2/2012 | Lim et al. |
| 2012/0053113 | A1 | 3/2012 | Bairstow et al. |
| 2014/0206844 | A1 | 7/2014 | Lim |
| 2015/0361127 | A1 | 12/2015 | Lim |

FOREIGN PATENT DOCUMENTS

| CN | 101160133 A | 4/2008 |
| EP | 0367090 A1 | 5/1990 |
| EP | 2664337 A1 | 11/2013 |
| JP | H09-503775 A | 4/1997 |
| JP | 2003-40775 A | 2/2003 |
| JP | 2003-292459 A | 10/2003 |
| JP | 2005-531521 A | 10/2005 |
| JP | 2006-520390 A | 9/2006 |
| JP | 2007-515397 A | 6/2007 |
| WO | WO-01/63280 A2 | 8/2001 |
| WO | WO-02/30983 A2 | 4/2002 |
| WO | WO-02/32406 A2 | 4/2002 |
| WO | WO-03/082247 A2 | 10/2003 |
| WO | WO-2004/082615 A2 | 9/2004 |
| WO | WO-2005/030252 A1 | 4/2005 |
| WO | WO 2005/046587 | * 5/2005 |
| WO | WO-2005/046587 A2 | 5/2005 |
| WO | WO-2005/121163 A2 | 12/2005 |
| WO | WO-2007/038686 A2 | 4/2007 |
| WO | WO-2008/067655 A1 | 6/2008 |
| WO | WO-2009/154695 A1 | 12/2009 |
| WO | WO-2010/068308 A1 | 6/2010 |
| WO | WO-2014/039987 A2 | 3/2014 |
| WO | WO-2014/113659 A1 | 7/2014 |

OTHER PUBLICATIONS

Atmani et al., "Role of inter-alpha-inhibitor and its related proteins in urolithiasis. Purification of an inter-alpha-inhibitor related protein from the bovine kidney," Urol Res. 27(1):57-61 (1999).
Bogdan et al., "Tumor necrosis factor-alpha contributes to apoptosis in hippocampal neurons during experimental group B streptococcal meningitis," J Infect Dis. 176(3):693-7 (1997).
Bradding et al., "TNF alpha is localized to nasal mucosal mast cells and is released in acute allergic rhinitis," Clin Exp Allergy. 25(5):406-15 (1995) (Abstract only provided) (1 page).
Carrette et al., "Purification and characterization of pig inter-alpha-inhibitor and its constitutive heavy chains," Biochim Biophys Acta. 1338(1):21-30 (1997).
Cazzola et al., "Emerging anti-inflammatory strategies for COPD," Eur Respir J. 40(3):724-41 (2012).
Daveau et al., "Human inter-alpha-inhibitor family in inflammation: simultaneous synthesis of positive and negative acute-phase proteins," Biochem J. 292(Pt 2):485-92 (1993).
de la Motte et al., "Mononuclear leukocytes bind to specific hyaluronan structures on colon mucosal smooth muscle cells treated with polyinosinic acid:polycytidylic acid: inter-alpha-trypsin inhibitor is crucial to structure and function," Am J Pathol. 163(1):121-33 (2003).

(Continued)

*Primary Examiner* — Shulamith H Shafer
(74) *Attorney, Agent, or Firm* — Clark & Elbing LLP

(57) ABSTRACT

The present invention generally provides processes for purification of Inter-alpha inhibitor proteins (IαIp) and compositions thereof from blood.

18 Claims, 13 Drawing Sheets

(56) References Cited

OTHER PUBLICATIONS

Feldmann et al., "Lasker Clinical Medical Research Award. TNF defined as a therapeutic target for rheumatoid arthritis and other autoimmune diseases," Nat Med. 9(10):1245-50, 1433 (2003).
Hoffer et al., "Improved virus safety and purity of a chromatographically produced Factor IX concentrate by nanofiltration," J Chromatogr B Biomed Appl. 669(2):187-96 (1995).
Ito et al., "A pilot randomized trial of a human anti-interleukin-6 receptor monoclonal antibody in active Crohn's disease," Gastroenterology. 126(4):989-96 (2004).
Iwasaki et al., "TNF-alpha contributes to the development of allergic rhinitis in mice," J Allergy Clin Immunol. 112(1):134-40 (2003).
Josic et al., "Proteomic characterization of inter-alpha inhibitor proteins from human plasma," Proteomics. 6(9):2874-85 (2006).
Katz, "Advances in the medical therapy of inflammatory bowel disease," Curr Opin Gastroenterol. 18(4):435-40 (2002).
Lim et al., "Affinity purification and enzymatic cleavage of inter-alpha inhibitor proteins using antibody and elastase immobilized on CIM monolithic disks," J Chromatogr A. 1065(1):39-43 (2005).
Lim et al., "Correlation between mortality and the levels of inter-alpha inhibitors in the plasma of patients with severe sepsis," J Infect Dis. 188(6):919-26 (2003).
Lim, "Inter-alpha inhibitors: From laboratory to market," <http://www.brownenterpriseforum.org/matriarch/documents/Lim.pdf>, retrieved Jul. 13, 2011.
Ljung et al., "Infliximab in inflammatory bowel disease: clinical outcome in a population based cohort from Stockholm County," Gut. 53(6):849-53 (2004).
MEGA- and GIGA preps of cosmid-, BAC-, PAC, YAC-, and P1-DNA with JETSTAR 2.0, Sep. 2005 (6 pages).
Michalski et al., "Preparation and properties of a therapeutic inter-alpha-trypsin inhibitor concentrate from human plasma," Vox Sang. 67(4):329-36 (1994).
Mihara et al., "IL-6/IL-6 receptor system and its role in physiological and pathological conditions," Clin Sci (Lond). 122(4):143-59 (2012).
Mizon et al., "Human pre-alpha-inhibitor: isolation from a by-product of industrial scale plasma fractionation and structural analysis of its H3 heavy chain," J Chromatogr B Biomed Sci Appl. 692(2):281-91 (1997).
Mo et al., "Anti-tumor necrosis factor-alpha treatment reduces allergic responses in an allergic rhinitis mouse model," Allergy. 66(2):279-86 (2011).
Odum, "Inter-alpha-trypsin inhibitor and pre-alpha-trypsin inhibitor in health and disease. Determination by immunoelectrophoresis and immunoblotting," Biol Chem Hoppe Seyler. 371:1153-8 (1990).
Opal et al., "Inter-alpha-inhibitor proteins are endogenous furin inhibitors and provide protection against experimental anthrax intoxication," Infect Immun. 73(8):5101-5 (2005).
Opal et al., "Longitudinal studies of inter-alpha inhibitor proteins in severely septic patients: a potential clinical marker and mediator of severe sepsis," Crit Care Med. 35(2):387-92 (2007).
Rutgeerts et al., "Optimizing anti-TNF treatment in inflammatory bowel disease," Gastroenterology. 126(6):1593-610 (2004).
Salier et al., "Inter-alpha-trypsin-inhibitor (ITI): use of immunoadsorbents for preparation of anti-ITI antiserum, ITI-free human serum and purified ITI," J Immunol Methods. 47(2):239-48 (1981).
Salier et al., "Purification of the human serum inter-alpha-trypsin inhibitor by zinc chelate and hydrophobic interaction chromatographies," Anal Biochem. 109(2):273-83 (1980).
Salier et al., "The inter-alpha-inhibitor family: from structure to regulation," Biochem J. 315(Pt 1):1-9 (1996).
Saukkonen et al., "The role of cytokines in the generation of inflammation and tissue damage in experimental gram-positive meningitis," J Exp Med. 171(2):439-48 (1990).
Singh et al., "Inter-alpha inhibitor protein administration improves survival from neonatal sepsis in mice," Pediatr Res. 68(3):242-7 (2010).
Sykes et al., "Treatment of severe autoimmune disease by stem-cell transplantation," Nature. 435(7042):620-7 (2005).
Takeuchi et al., "Baseline tumour necrosis factor alpha levels predict the necessity for dose escalation of infliximab therapy in patients with rheumatoid arthritis," Ann Rheum Dis. 70(7):1208-15 (2011) (8 pages).
Tanaka et al., "Targeting interleukin-6: all the way to treat autoimmune and inflammatory diseases," Int J Biol Sci. 8(9):1227-36 (2012).
Tarner et al., "Treatment of autoimmune disease by adoptive cellular gene therapy," Ann NY Acad Sci. 998:512-9 (2003).
van Heel et al., "Inflammatory bowel disease is associated with a TNF polymorphism that affects an interaction between the OCT1 and NF(-kappa)B transcription factors," Hum Mol Genet. 11(11):1281-9 (2002).
Wu et al., "Delayed administration of human inter-alpha inhibitor proteins reduces mortality in sepsis," Crit Care Med. 32(8):1747-52 (2004).
Yang et al., "Administration of human inter-alpha-inhibitors maintains hemodynamic stability and improves survival during sepsis," Crit Care Med. 30(3):617-22 (2002).
Communication Pursuant to Article 94(3) EPC in European Patent Application No. 09767008.7 dated Oct. 22, 2013 (7 pages).
Communication Pursuant to Rules 70(2) and 70a(2) EPC for European Patent Application No. 09767008.7, dated Aug. 12, 2011 (1 page).
English Translation of Notification of Reason for Refusal in Japanese Patent Application No. 2011-511643, mailed on Nov. 12, 2013 (7 pages).
Examination Report for Australian Patent Application No. 2009260822, dated Dec. 19, 2014 (4 pages).
Extended European Search Report for European Application No. EP 09767008.7, dated Jul. 26, 2011 (7 pages).
First Office Action for Chinese Patent Application No. 200980129119.6, dated Apr. 7, 2013 (31 pages)
International Preliminary Report on Patentability and Written Opinion of the International Searching Authority for International Application No. PCT/US2009/003291, dated Nov. 30, 2010 (6 pages).
International Search Report for International Application No. PCT/US2004/036848, mailed Nov. 4, 2005 (5 pages).
International Search Report for International Application No. PCT/US2009/003291, mailed Aug. 24, 2009 (2 pages).
Supplementary European Search Report for European Patent Application No. 04810367, dated Jan. 18, 2010 (7 pages).
English Translation of the Notification of Reason for Refusal for Japanese Patent Application No. 2015-080358, mailed Mar. 30, 2016 (5 pages).
Notice of Preliminary Rejection for Korean Patent Application No. 10-2010-7029406, dated Oct. 30, 2015 (14 pages).
Ahmed et al., "Inhibition of allergic late airway responses by inhaled heparin-derived oligosaccharides," J Appl Physiol (1985). 88(5):1721-9 (2000).
Ahmed et al., "Prevention of exercise-induced bronchoconstriction by inhaled low-molecular-weight heparin," Am J Respir Crit Care Med. 160(2):576-81 (1999).
Brass et al., "Chronic LPS inhalation causes emphysema-like changes in mouse lung that are associated with apoptosis," Am J Respir Cell Mol Biol. 39(5):584-90 (2008).
Campo et al., "Molecular-weight-dependent effects of nonanticoagulant heparins on allergic airway responses," J Appl Physiol (1985). 86(2):549-57 (1999).
Communication Pursuant to Article 94(3) EPC in European Patent Application No. 04810367.5, dated Jul. 1, 2013 (5 pages).
Communication Pursuant to Article 94(3) EPC in European Patent Application No. 04810367.5, dated May 23, 2014 (5 pages).
Communication Pursuant to Article 94(3)EPC for European Patent Application No. 09767008.7, dated Sep. 23, 2014 (6 pages).
Decision of Refusal for Japanese Patent Application No. 2011-511643, mailed Dec. 9, 2014 (4 pages).

(56) References Cited

OTHER PUBLICATIONS

Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther. 328(3):758-65 (2009).
Enghild et al., "Analysis of inter-alpha-trypsin inhibitor and a novel trypsin inhibitor, pre-alpha-trypsin inhibitor, from human plasma. Polypeptide chain stoichiometry and assembly by glycan," J Biol Chem. 264(27):15975-81 (1989).
EPO Communication pursuant to Rule 112(1) EPC for European Patent Application No. 09767008.7, dated Aug. 11, 2015 (3 pages).
Extended European Search Report and Written Opinion for European Patent Application No. 09767008.7, dated Jul. 26, 2011 (7 pages).
Fourth Office Action for Chinese Patent Application No. 200980129119.6, issued Jul. 30, 2015 (19 pages).
Garantziotis et al., "Inter-alpha-trypsin inhibitor attenuates complement activation and complement-induced lung injury," J Immunol. 179(6):4187-92 (2007) (7 pages).
Hamm et al., "Frequent expression loss of Inter-alpha-trypsin inhibitor heavy chain (ITIH) genes in multiple human solid tumors: a systematic expression analysis," BMC Cancer. 8:25 (2008) (15 pages).
International Preliminary Report on Patentability and Written Opinion of the International Searching Authority for International Application No. PCT/US2013/058791, mailed Jun. 11, 2015 (7 pages).
International Preliminary Report on Patentability and Written Opinion of the International Searching Authority for International Application No. PCT/US2014/012033, issued Jul. 21, 2015 (10 pages).
International Search Report and Written Opinion for International Application No. PCT/US2014/012033, mailed May 27, 2014 (14 pages).
International Search Report and Written Opinion for International Patent Application No. PCT/US2013/058791, mailed Jan. 10, 2014 (11 pages).
Katoh et al., "Galectin-9 inhibits CD44-hyaluronan interaction and suppresses a murine model of allergic asthma," Am J Respir Crit Care Med. 176(1):27-35 (2007).
Koraka et al., "Plasma levels of inter-alpha inhibitor proteins in children with acute Dengue virus infection," PLoS One. 5(4):e9967 (2010) (4 pages).
Kricka, "Human anti-animal antibody interferences in immunological assays," Clin Chem. 45(7):942-956 (1999).
Martinez-Salas et al., "Inhibition of allergic airway responses by inhaled low-molecular-weight heparins: molecular-weight dependence," J Appl Physiol (1985). 84(1):222-8 (1998).
Molinari et al., "Inhibition of antigen-induced airway hyperresponsiveness by ultralow molecular-weight heparin," Am J Respir Crit Care Med. 157(3 Pt 1):887-93 (1998).
Odum, "Inter-alpha-trypsin inhibitor: a plasma proteinase inhibitor with a unique chemical structure," Int J Biochem. 22(9):925-30 (1990).
Office Action for Canadian Patent Application No. 2544816, dated Dec. 30, 2013 (4 pages).
Office Action for Canadian Patent Application No. 2544816, dated Mar. 1, 2012 (7 pages).
Office Action for Canadian Patent Application No. 2544816, dated Oct. 20, 2014 (6 pages).
Office Action for Canadian Patent Application No. 2726281, dated Jun. 30 2015 (9 pages).
Raoust et al., "Pseudomonas aeruginosa LPS or flagellin are sufficient to activate TLR-dependent signaling in murine alveolar macrophages and airway epithelial cells," PLoS One. 4(10):e7259 (2009) (9 pages).
Sanon et al., "Peripheral arterial ischemic events in cancer patients," Vasc Med. 16(2):119-30 (2011).
Second Office Action for Chinese Patent Application No. 200980129119.6, issued Feb. 20, 2014 (19 pages).
Second Office Action for Chinese Patent Application No. 201210460374.2, dated Aug. 22, 2014 (11 pages).
Sin et al., "Chronic obstructive pulmonary disease as a risk factor for cardiovascular morbidity and mortality," Proc Am Thorac Soc. 2(1):8-11 (2005).
Su et al., "Role of CFTR expressed by neutrophils in modulating acute lung inflammation and injury in mice," Inflamm Res. 60(7):619-32 (2011).
Third Office Action for Chinese Patent Application No. 200980129119.6, mailed on Nov. 15, 2014 (21 pages).
Trefz et al., "Establishment of an enzyme-linked immuno-sorbent assay for urinary trypsin inhibitor by using a monoclonal antibody," J Immunoassay. 12(3):347-69 (1991).
Triantaphyllopoulos et al., "A model of chronic inflammation and pulmonary emphysema after multiple ozone exposures in mice," Am J Physiol Lung Cell Mol Physiol. 300(5):L691-700 (2011).
Verhein et al., "IL-1 receptors mediate persistent, but not acute, airway hyperreactivity to ozone in guinea pigs," Am J Respir Cell Mol Biol. 39(6):730-8 (2008).
Zhuo et al., "Defect in SHAP-hyaluronan complex causes severe female infertility. A study by inactivation of the bikunin gene in mice," J Biol Chem. 276(11):7693-6 (2001) (5 pages).
Zosky et al., "Animal models of asthma," Clin Exp Allergy. 37(7):973-88 (2007).
Burnouf, "Chromatography in plasma fractionation: benefits and future trends," J Chromatogr B Biomed Appl. 664(1):3-15 (1995).
Odum, "Inter-alpha-trypsin inhibitor and pre-alpha-trypsin inhibitor in health and disease. Determination by immunoelectrophoresis and immunoblotting," Biol Chem Hoppe Seyler. 371(12):1153-8 (1990).
McCann, et al. "Evaluation of expanded bed adsorption chromatography for extraction of prothrombin complex from Cohn Supernatant I," Biologicals. 36(4):227-233 (2008).
Partial Supplementary European Search Report for European Application No. 14740523.7, dated Jun. 8, 2016 (7 pages).
Examination Report for Australian Patent Application No. 2009260822, issued Aug. 23, 2016 (3 pages).
Office Action for Canadian Patent Application No. 2726281, dated Aug. 10, 2016 (4 pages).
Communication Pursuant to Article 94(3) EPC in European Patent Application No. 09767008.7 dated Apr. 28, 2016 (7 pages).
Office Action for Chinese Patent Application No. 201210460374.2, dated Jan. 24, 2014 (5 pages).
Communication Pursuant to Article 94(3) and Rule 71(1) EPC in European Patent Application No. 04810367.5 dated Jun. 4, 2012 (2 pages).
Bove, "Anaphylactic reaction to purified anti-hemophilic factor concentrate," Transfusion 28(6):603 (1988).

\* cited by examiner

FIG. 1B

Cryo-poor Plasma or
Intermediate Plasma Fractions

↓ Solvent/Detergent

DEAE-CIM

↙ ↓

Flow through  Bound

↓

Salt buffer wash

↓

Low pH wash

↓

Elution

↓

Ultrafiltration or
Diafiltration

↓

Nanofiltration

↓

Lyophilization

FIG. 6F  SM  W#1  W#2  EL

SDS PAGE of purification of Intermediate Plasma Fraction D
Std MW = Standard Molecular Weight Proteins
pH wash = Wash buffer pH 2.95
Salt Wash = Wash buffer containing 290 mM NaCl
Elution = Elution buffer containing 1000 mM NaCL.
Arrows — 250 kDa Inter-alpha Inhibitor and 125 kDa Pre alpha Inhibitor

PREPARATION AND COMPOSITION OF INTER-ALPHA INHIBITOR PROTEINS FROM BLOOD

CROSS-REFERENCE TO RELATED APPLICATION

This application claims the benefit of U.S. Provisional Application No. 61/130,269, filed on May 28, 2008, the entire contents of which are incorporated herein by reference.

STATEMENT OF RIGHTS TO INVENTIONS MADE UNDER FEDERALLY SPONSORED RESEARCH

This work was supported by National Institutes of Health/National Institute of General Medical Sciences Grants, Grant Nos. 2R44GM65667-02 and 1R43GM079071-01A1. The government has certain rights in the invention.

BACKGROUND OF THE INVENTION

Sepsis and Systemic Inflammatory Response Syndrome (SIRS), both refer to a severe biochemical reaction following exposure to an infectious agent (e.g. bacterial toxin such as Anthrax), or from injury or trauma. The systemic response can lead to septic shock, which is characterized by a precipitous drop in blood pressure, cardiovascular collapse, and/or multiple organ failure. Despite the introduction of antibiotics over fifty years ago, the mortality rate among subjects diagnosed with septic shock is 30-50%, higher than that of breast, colon, or prostate cancer. There are approximately 800,000 sepsis cases per year in the U.S. at a cost of $17 billion, with an equal number in the rest of the world. Sepsis and SIRS are increasing rapidly throughout the world due to antibiotic resistance and increased biological threats. The "at risk" population is substantially greater when one considers the potential implications worldwide pandemics (e.g., bird flu) or bioterrorism. In bioterrorism or in battlefield exposure the mortality rates are expected to be much higher. Rapidly and reliably treating sepsis, SIRS, and septic shock has been difficult using conventional medications.

The inter-alpha inhibitor protein (IαIp) family is a group of plasma-associated serine protease inhibitors that modulate the body's response toward the severe systemic inflammation accompanying sepsis, infection, trauma, and injury. Inter-alpha inhibitor protein (IαIp) has been shown to improve the survival or condition of test animals suffering from sepsis; infected with anthrax, Ebola, or Dengue virus; or suffering from lung injury due to exposure to toxic chemicals or ionizing radiation. IαIp is a large protein that is isolated from blood. Because of the therapeutic use of inter-alpha inhibitor proteins in treating sepsis and SIRS, methods for purifying or preparing IαIp are urgently required.

SUMMARY OF THE INVENTION

As described below, the present invention relates to a method for the purification of inter-alpha inhibitor proteins (IαIp) and their use for treatment of disease or symptoms thereof, including diseases such as sepsis, acute inflammatory diseases, severe shock, septic shock, rheumatoid arthritis, cancer, cancer metastasis, infectious diseases, and preterm labor; or reducing the risk of mortality associated with sepsis, acute inflammatory diseases, severe shock, septic shock, rheumatoid arthritis, cancer, cancer metastasis, infectious diseases, and preterm labor.

In one aspect, the invention provides a method for purifying an inter-alpha inhibitor protein (IαIp protein), the method involving a step wherein the IαIp protein is exposed to conditions of pH of about 4.0 or lower (e.g., 3.7, 3.5, 3.4, 3.3, 3.1, 3.0, 2.9, 2.0).

In one aspect, the invention provides a composition containing an IαIp protein purified according to a method involving a step wherein the IαIp protein is exposed to conditions of pH of about 4.0 or lower In another aspect, the invention provides a pharmaceutical composition containing an effective dose of an IαIp protein purified according to a method involving a step wherein the IαIp protein is exposed to conditions of pH of about 4.0 or lower and a pharmaceutically acceptable excipient.

In yet another aspect, the invention provides a method for treating or preventing disease or disease symptoms in a subject comprising administering to the subject a composition containing an IαIp protein purified according to a method involving a step wherein the IαIp protein is exposed to conditions of pH of about 4.0 or lower In still another aspect, the invention provides a kit for purifying an IαIp protein having at least one buffer solution with a pH of about 4.0 or lower and instructions for using the kit. In one embodiment the kit has at least one buffer solution that is a wash buffer with a pH of about 4.0 or lower. In another embodiment, the kit of has at least two buffer solutions that are wash buffers with a pH of about 4.0 or lower. In a specific embodiment, a first wash buffer has a pH of about 4.0 and a second wash buffer has a pH of about 3.3. In another specific embodiment, a first wash buffer has a pH of about 4.0 and a second wash buffer has a pH of about 2.9.

In an additional aspect, the invention provides a kit for therapeutic use having a composition containing an IαIp protein purified according to a method involving a step wherein the IαIp protein is exposed to conditions of pH of about 4.0 or lower.

In an additional aspect, the invention provides a kit for analytical use having a composition containing an IαIp protein purified according to a method involving a step wherein the IαIp protein is exposed to conditions of pH of about 4.0 or lower.

In a related aspect, the invention provides a method for purifying an inter-alpha inhibitor protein (IαIp protein), the method involving: placing blood, a blood plasma fraction, or an intermediate plasma fraction on a chromatography column, subjecting the column to a wash buffer with a pH of about 4.0 or lower.

In yet another related aspect, the invention provides a purified inter-alpha inhibitor protein (IαIp protein) made by a method involving a step wherein the IαIp protein is exposed to conditions of pH of about 4.0 or lower and wherein the IαIp protein achieves increased binding in a competitive Enzyme-Linked Immunosorbent Assay (ELISA) compared to a reference. In one embodiment, the binding of the IαIp protein is increased by greater than 1-, 1.5-, 2-, 3-, 4-, 5-, or 10-fold compared to the reference (e.g., IαIp protein not treated with low pH).

In various embodiments of any of the above aspects or of any other invention delineated herein, the method involves a step wherein the IαIp protein is exposed to conditions of pH of about 3.6 or lower. In various embodiments, the method involves a step wherein the IαIp protein is exposed to conditions of pH of about 3.3 or lower. In various embodiments, the method involves a step wherein the IαIp protein is exposed to conditions of pH between about 3.3 to about 3.1. In various embodiments, the method involves a step wherein the IαIp protein is exposed to conditions of pH between about 3.1 to about 2.9.

In various embodiments of any of the above aspects or of any other invention delineated herein, the method involves a chromatography step or solid phase extraction step. In various embodiments, the chromatography step comprises liquid chromatography, column chromatography, anion-exchange chromatography, or a combination thereof. In various embodiments, the chromatography involves the use of a monolithic support or particle-based support. In various embodiments, the monolithic support or particle support involves an immobilized anion-exchange ligand. In various embodiments, the immobilized anion-exchange ligand is a diethylaminoethane (DEAE) or a quaternary amine (Q).

In various embodiments of any of the above aspects or of any other invention delineated herein, the method involves at least one buffer wash step, wherein the wash buffer of at least one buffer wash step has a pH of about 4.0 or lower. In various embodiments, the method involves at least one buffer wash step, wherein the wash buffer of at least one buffer wash step has a pH of about 3.6 or lower. In various embodiments, the method involves at least one buffer wash step, wherein the wash buffer of at least one buffer wash step has a pH of about 3.3 or lower. In various embodiments, the method involves at least one buffer wash step, wherein the wash buffer of at least one buffer wash step has a pH of about 3.1 or lower. In various embodiments, the method involves at least one buffer wash step, wherein the wash buffer of at least one buffer wash step has a pH between about 3.1 to about 2.9. In various embodiments, the inter-alpha inhibitor protein (IαIp protein) binds to the column. In various embodiments the inter-alpha inhibitor protein (IαIp protein) is isolated.

In various embodiments of any of the above aspects or of any other invention delineated herein, the method involves a step where the IαIp protein is exposed to concentrations of salt at about 250 mM NaCl or higher (e.g., 260, 270, 280, 290 mM NaCl). In various embodiments of any of the above aspects delineated herein, the method involves at least one buffer wash step, where the wash buffer has a concentration of salt at about 250 mM NaCl or higher (e.g., 260, 270, 280, 290 mM NaCl).

In various embodiments of any of the above aspects or of any other invention delineated herein, the IαIp protein is purified from blood. In various embodiments, the IαIp protein is purified from blood plasma or a blood plasma fraction. In various embodiments, the blood plasma is cryo-poor plasma or the blood plasma fraction is an intermediate plasma fraction. In various embodiments, the intermediate plasma fraction is an IαIp containing fraction. In various embodiments, the blood, blood plasma fraction, or intermediate plasma fraction is human, primate, bovine, equine, porcine, ovine, feline, canine, or combinations thereof.

In various embodiments of any of the above aspects or of any other invention delineated herein, the IαIp protein has an apparent molecular weight of between about 60 to about 280 kDa. In various embodiments of any of the above aspects or of any other invention delineated herein, the IαIp protein or composition has a purity ranging from about 85% to about 100% pure. In various embodiments of any of the above aspects or of any other invention delineated herein, the IαIp protein or composition has a yield ranging from about 85% to about 100%. In some embodiments, the IαIp protein or composition can be used for an analytical use (e.g., to quantitate the amount of IαIp in a sample of unknown IαIp concentration). In some embodiments, the IαIp protein or composition has biological activity. In various embodiments, the biological activity is a cytokine inhibitor activity, chemokine inhibitor activity, or serine protease inhibitor activity. In various embodiments, the method involves a viral inactivation step or nanofiltration step either before or after the chromatography step.

In various embodiments of any of the above aspects or of any other invention delineated herein, the composition or pharmaceutical composition is for the treatment in a subject in need thereof. In various embodiments, the subject is identified as in need of treatment with the composition. In various embodiments, the subject is identified as in need of treatment for acute inflammatory disease, sepsis, severe shock, septic shock, rheumatoid arthritis, cancer, cancer metastasis, trauma/injury, infectious disease, or preterm labor. In various embodiments of any of the above aspects, the subject in need thereof is human, primate, bovine, equine, porcine, ovine, feline, or canine.

The invention provides methods of preparing or purifying inter-alpha inhibitor proteins (IαIp) from blood plasma. Other features and advantages of the invention will be apparent from the detailed description, and from the claims.

Definitions

As used herein, "alteration" is meant a change (increase or decrease) in the yield, quantity, concentration, activity, purity, or levels of an IαIp protein as detected by standard art known methods such as those described herein. As used herein, an alteration includes a 10% change in yield, purity, or activity, preferably a 25% change, more preferably a 40% change, and most preferably a 50% or greater change in expression levels.

By "analog" is meant a structurally related polypeptide or nucleic acid molecule having the function of a reference polypeptide or nucleic acid molecule.

By "compound" is meant any small molecule chemical compound, antibody, nucleic acid molecule, or polypeptide, or fragments thereof.

By "reduces" or "increases" is meant a negative or positive alteration, respectively, of at least 10%, 25%, 50%, 75%, or 100%.

By "subject" is meant a mammal, including, but not limited to, a human or non-human mammal, such as a primate, bovine, equine, porcine, ovine, feline, or canine.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIGS. 1A-1B depict schemes for the purification of IαIp from human plasma using a single chromatographic step. FIG. 1A depicts a scheme for the purification of IαIp from human plasma using a low pH wash step. FIG. 1B depicts a scheme for the purification of IαIp from human plasma using a salt buffer wash step and a low pH wash step.

FIG. 2A shows a UV trace of plasma (1 mL of 1:100 dilution in 25 mM Tris, 200 mM NaCl, pH 7.8) separated by DEAE chromatography (monolithic support; flow rate: 5 mL/min) with one wash step with a wash buffer (25 mM Tris, 200 mM NaCl, pH 7.8) and eluted with elution buffer (100 mM Tris, 1000 mM NaCl, pH 7.6). FIG. 2B shows a UV trace of plasma (1 mL of 1:100 dilution in 25 mM Tris, 200 mM NaCl, pH 7.8) separated by DEAE chromatography (monolithic support; flow rate: 5 mL/min) with one wash step using a low pH wash buffer (150 mM Acetic Acid, pH 4.0) and eluted with elution buffer (100 mM Tris, 1000 mM NaCl, pH 7.6). FIG. 2C shows a UV trace of plasma (1 mL of 1:100 dilution in 25 mM Tris, 200 mM NaCl, pH 7.8) separated by DEAE chromatography (monolithic support; flow rate: 5 mL/min) with one wash step using a low pH wash buffer (150 mM Acetic Acid, pH 3.3) and eluted with elution buffer (100 mM Tris, 1000 mM NaCl, pH 7.6).

FIG. 4A shows a UV trace of intermediate plasma (1 mL of 1:200 dilution of Fraction D in 25 mM Tris, 200 mM NaCl, pH 7.8) separated by DEAE chromatography (monolithic support; flow rate: 5 mL/min) with one wash step using a low pH wash buffer (Wash Buffer #1: 150 mM Acetic Acid, pH 4.0) and eluted with elution buffer (100 mM Tris, 1000 mM NaCl, pH 7.6). FIG. 4B shows a UV trace of intermediate plasma fraction (1 mL of 1:200 dilution of Fraction C in 25 mM Tris, 200 mM NaCl, pH 7.8) separated by DEAE chromatography (1 mL monolithic support; flow rate: 5 mL/min) with with one wash step using a low pH wash buffer (Wash Buffer #1: 150 mM Acetic Acid, pH 4.0) and eluted with elution buffer (100 mM Tris, 1000 mM NaCl, pH 7.6). FIG. 4C shows a UV trace of intermediate plasma (1 mL of 1:200 dilution of Fraction D in 25 mM Tris, 200 mM NaCl, pH 7.8) separated by DEAE chromatography (1 mL monolithic support; flow rate: 5 mL/min) with two wash steps using two low pH wash buffers (Wash Buffer #1: 150 mM Acetic Acid, pH 4.0; Wash Buffer #2: 200 mM Acetic Acid, pH 3.3) and eluted with elution buffer (100 mM Tris, 1000 mM NaCl, pH 7.6). FIG. 4D shows a UV trace of intermediate plasma fraction (1 mL of 1:200 dilution of Fraction C in 25 mM Tris, 200 mM NaCl, pH 7.8) separated by DEAE chromatography (1 mL monolithic support; flow rate: 5 mL/min) with two wash steps using two low pH wash buffers (Wash Buffer #1: 150 mM Acetic Acid, pH 4.0; Wash Buffer #2: 200 mM Acetic Acid, pH 3.3) and eluted with elution buffer (100 mM Tris, 1000 mM NaCl, pH 7.6).

FIGS. 6A-6F show that the purification of IαIp protein from cryo-poor plasma or intermediate plasma (Fraction D and Fraction C) by DEAE chromatography using two low pH wash steps (pH 4.0 and pH 3.3) is scalable. FIG. 6A shows a UV trace of cryo-poor plasma (Starting material: 25 mL of 1:10 dilution of Fraction C in 25 mM Tris, 200 mM NaCl, pH 7.8) separated by DEAE chromatography (8 mL monolithic support; flow rate: 40 mL/min) with two wash steps using two low pH wash buffers (Wash Buffer #1: 150 mM Acetic Acid, pH 4.0; Wash Buffer #2: 200 mM Acetic Acid, pH 3.3) and eluted with elution buffer (100 mM Tris, 1000 mM NaCl, pH 7.6). FIG. 6B shows fractions from the separation of cryo-poor plasma by DEAE monolithic chromatography (Starting material (SM), Wash #1 (W#1), Wash #2 (W#2), and Eluate (EL)) analyzed by SDS-PAGE (4-20% gradient). FIG. 6C shows a UV trace of intermediate plasma (Starting material: 2 mL of 1:125 dilution of Fraction D in 25 mM Tris, 200 mM NaCl, pH 7.8) separated by DEAE chromatography (8 mL monolithic support; flow rate: 40 mL/min) with two wash steps using two low pH wash buffers (Wash Buffer #1: 150 mM Acetic Acid, pH 4.0; Wash Buffer #2: 200 mM Acetic Acid, pH 3.3) and eluted with elution buffer (100 mM Tris, 1000 mM NaCl, pH 7.6). FIG. 6D shows fractions from the separation of intermediate plasma (Fraction D) by DEAE monolithic chromatography (Starting material (SM), Wash #1 (W#1), Wash #2 (W#2), and Eluate (EL)) analyzed by SDS-PAGE (4-20% gradient). FIG. 6E shows a UV trace of intermediate plasma fraction (Starting material: 2 mL of 1:125 dilution of Fraction C in 25 mM Tris, 200 mM NaCl, pH 7.8) separated by DEAE chromatography (8 mL monolithic support; flow rate: 40 mL/min) with two wash steps using two low pH wash buffers (Wash Buffer #1: 150 mM Acetic Acid, pH 4.0; Wash Buffer #2: 200 mM Acetic Acid, pH 3.3) and eluted with elution buffer (100 mM Tris, 1000 mM NaCl, pH 7.6). FIG. 6F shows fractions from the separation of intermediate plasma (Fraction C) by DEAE monolithic chromatography (Starting material (SM), Wash #1 (W#1), Wash #2 (W#2), and Eluate (EL)) analyzed by SDS-PAGE (4-20% gradient).

FIG. 7A shows a UV trace of cryo-poor plasma (12.5 column volumes of 1:10 dilution in 40 mM Tris, 200 mM NaCl, pH 7.6; 0.2 μM filtered) separated by DEAE chromatography (monolithic support) with two wash steps using a salt wash buffer (10 column volumes of 40 mM Tris-HCl, 290 mM NaCl pH 7.6) and a low pH wash buffer (10 column volumes of 200 mM Na-Acetate pH 2.95) and eluted with high salt elution buffer (5 column volumes of 40 mM Na-Citrate pH 6.50, 1000 mM NaCl). FIG. 7B shows a UV trace of intermediate plasma fraction (Fraction D) (2.5 column volumes, 1:10 dilution in 40 mM Tris, 200 mM NaCl, pH 7.6; 0.2 µM filtered) separated by DEAE chromatography (monolithic support) with two wash steps using a salt wash buffer (10 column volumes of 40 mM Tris-HCl, 290 mM NaCl pH 7.6) and a low pH wash buffer (10 column volumes of 200 mM Na-Acetate pH 2.95) and eluted with high salt elution buffer (5 column volumes of 40 mM Na-Citrate pH 6.50, 1000 mM NaCl). A commercially available 8 mL DEAE monolithic column (DEAE-CIM; BIA Separations) at a flow rate of 2.5 column volumes (cv) per minute was used to perform the chromatography. The flowthrough was collected. Additional loading buffer was applied to the column until the flowthrough peak returned to baseline (e.g., in FIG. 7A, 7 column volumes 25 mM Tris, 200 mM NaCl, pH 7.6). All peaks eluted by the washes were collected. The peak eluted by the high salt elution buffer was collected and this fraction contained highly pure IαIp.

DETAILED DESCRIPTION OF THE INVENTION

Figure 1A:
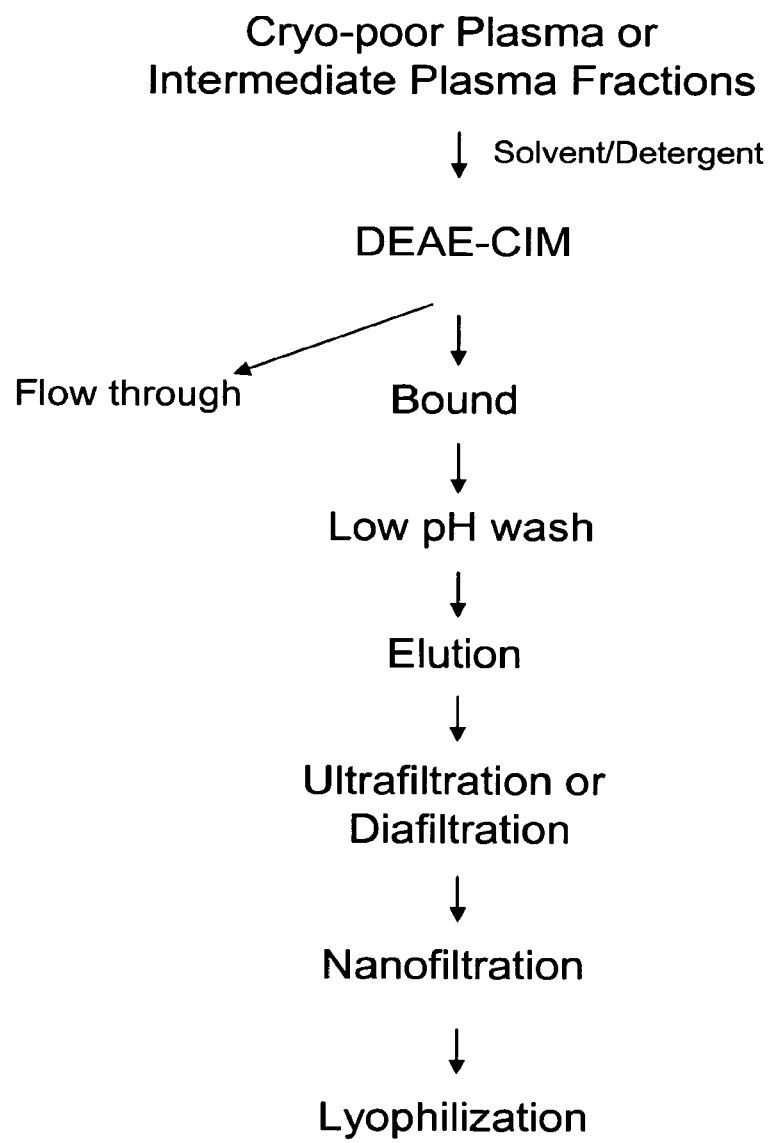

The present invention generally provides a method for purifying IαIp from plasma and therapeutic compositions for treating a disease, disorder, or injury characterized by acute inflammatory disease, sepsis, severe shock, septic shock, rheumatoid arthritis, cancer, cancer metastasis, infectious disease, and preterm labor. The method involves exposing IαIp to a low pH buffer during its purification.
Inter-Alpha Inhibitor Protein (IαIp)

As used herein, "Inter-alpha inhibitor proteins (IαIp)" refer to large, multi-component polypeptides in a family of structurally related serine protease inhibitors. By "polypeptide" is meant any chain of amino acids, regardless of length or post-translational modification. The complex has been shown to be important in the inhibition of an array of proteases including neutrophil elastase, plasmin, trypsin, chymotrypsin, cathepsin G, and acrosin including trypsin-type protease inhibitors. In human plasma, IαIp proteins are found at relatively high concentrations (400-800 mg/L). Unlike other inhibitor molecules, this family of inhibitors consists of a combination of polypeptide chains (light and heavy chains) covalently linked uniquely by a chondroitin sulfate chain.

The heavy chains of Inter-alpha proteins (H1, H2 and H3) are also called Hyaluronic acid (HA) binding proteins. The major forms found in human plasma are inter-alpha-inhibitor (IaI), which consists of two heavy chains (H1 & H2) and a single light chain (L), and pre-alpha-inhibitor (Pap, which consists of one heavy (H3) and one light chain (L). The light chain (also termed bikunin (bi-kunitz inhibitor) with two Kunitz domains) is known to broadly inhibit plasma serine proteases. IαI and PαI present in the plasma fraction have an apparent molecular weight of between about 60 kDa to about 280 kDa. Molecular weight may be determined by sodium dodecyl sulfate polyacrylamide gel electrophoresis (SDS-PAGE). IaI and PaI have also been found to be complexed with H4, another heavy chain of IαIp proteins. Without wishing to be bound by any particular scientific theory, it is believed that heavy chains of IαIp, after being released from the complex, bind (Hyaluronic acid) HA preventing HA from binding its receptor, CD44. In the absence of heavy chains of IαIp, HA will bind to CD44 and trigger the secretion of pro-inflammatory factors, for example, TNF-alpha, and cause inflammation. Meanwhile, the light chains of IαIp, once released from the complex exhibit anti-protease activity.
Sepsis and Systemic Inflammatory Response Syndrome (SIRS)

Sepsis, and Systemic Inflammatory Response Syndrome (SIRS), both refer to a severe physiochemical reaction following exposure to an infectious agent (e.g., bacterial toxin such as Anthrax), or trauma/injury. Sepsis is an individual's over-reaction to an agent with potentially life-threatening consequences that do not typically arise directly from the causative agent. Sepsis, if untreated, can result in serious damage to living tissues that places a patient in danger of progression multiple organ dysfunction, shock and ultimately death.

Sepsis, SIRS, and septic shock are associated with activation of innate immunity and coagulation systems. Sepsis and septic shock are characterized clinically by systemic inflammation, coagulopathy, hypotension and multiple organ dysfunction (J.-L. Vincent et al., Annuals of Medicine 34 (2002) 606-613). During severe sepsis, a network of specific proteases activates clotting, fibrinolytic and complement factors. These proteases can also trigger tissue and organ damage and enhance non-specific proteolysis of clotting and complement factors in plasma (J. Wite et al., Intensive Care Medicine 8 (1982) 215-222; S. J. Weiss, New England Journal of Medicine 320 (1989) 365-376). "Sepsis-like" symptoms are observed in the exposed individuals mainly due to the overwhelming systemic inflammatory response of the body. The overreaction typically includes excessive production of cytokines ("cytokine storm") and destructive proteases and disturbances in metabolic, oxygenation, coagulation, and vascular functions leading to multi-organ dysfunction.

IαIp are natural blood proteins and are part of the body's innate immune system. IαIp modulates the body's response toward the severe systemic inflammation accompanying sepsis, infection, trauma and injury. IαIp are a vital natural defense against sepsis and SIRS and, as such, they modulate the body's defense against "overreaction" to the effects of systemic inflammation. IαIp are inhibitors of serine proteases, protein digesting enzymes involved in a wide variety of physiological processes including coagulation, inflammation and immune response. IαIp serve as a broad spectrum biological response modifier to regulate circulating levels of secreted inflammatory substances such as immune response regulators (cytokines), proteins that attract leukocytes to sites of injury or inflammation (chemokines), and destructive proteases that cause severe morbidity and excessive mortality in affected patients. IαIp proteins bind circulating cytokines, chemokines and proteases that cause and sustain the septic condition. During severe inflammatory processes, the body's level of IαIp is rapidly depleted resulting in an uncontrolled disease process. A highly significant, inverse relationship exists between plasma IαIp levels and the severity of disease and mortality in sepsis patients (Lim et al., J Infect Dis 2003, 188:919-926).

IαIp has been shown to significantly improve survival of experimental animals suffering from sepsis and those infected with anthrax as well as animals suffering from acute lung injury following exposure to toxic chemicals or ionizing radiation (Yang et al., Crit Care Med 2002, 30(3):617-622; Lim et al., J Infect Dis 2003, 188:919-926; Wu et al., Crit Care Med 2004, 32(8):1747-1752; and Opal et al., Infect and Immun 2005, 73(8):5101-5105). Therapeutic effects on coagulation, metabolism, liver injury, inflammatory cytokine, and oxygenation functions were independent of the stimuli or causative agents. In severe cases of acute inflammation when IαIp levels become severely depleted, it has demonstrated that progression to an uncontrolled disease process can be partially or completely prevented by exogenous administration of IαIp (Yang et al., Crit Care Med 2002, 30(3):617-622; Wu et al., Crit Care Med 2004, 32(8): 1747-1752). Circulating cytokines, chemokines, and proteases can be removed or inactivated by the administration of IαIp and this removal or inactivation results in improved survival, reduced morbidity and increased time to treat any underlying disease condition or infection. A protease fragment of IαIp isolated from urine has demonstrated significant efficacy in reducing mortality in septic patients (Lin H Y. Zhonghua Yi Xue Za Zhi. 2007 Feb. 13; 87(7):451-7). By restoring control, replacement therapy with IαIp has the potential to improve survival, reduce morbidity and provide time to treat the underlying disease condition or infection. Replacement therapy has a high safety margin because IαIp is normally present at relatively high levels in the blood. IαIp is a useful, safe agent for maintaining hemodynamic stability, preventing organ injury, and improving survival in sepsis patients and those exposed to "cytokine storm".

Therapeutic Methods

Disclosed herein is a therapeutic method for administration of purified IαIp to a subject to treat acute inflammatory disease, sepsis, severe shock, septic shock, rheumatoid arthritis, cancer, cancer metastasis, infectious disease, and preterm labor. The invention may be used for the treatment of virtually any disease associated with a decrease in Inter-alpha inhibitor protein (IαIp) levels in a subject. The decrease in Inter-alpha inhibitor proteins (IαIp) levels may be associated with an undesirable increase in chemokines, cytokines, or proteases. For example, the mammal may have a disease, disorder, or condition that results in an undesirable increase in chemokines, cytokines, or proteases. Exemplary treated conditions include acute inflammatory disease, sepsis, severe shock, septic shock, rheumatoid arthritis, cancer, cancer metastasis, trauma/injury, infectious disease, or preterm labor. In other embodiments, the mammal has an increased risk of developing a disease, disorder, or condition that is delayed or prevented by the method.

The methods of the invention involve the administration of IαIp in a therapeutically effective dose. In various embodiments, the method increases the level of IαIp in a subject by at least 5%, 10%, 25%, 50%, 75%, 100%, 200%, or even by as much as 300%, 400%, or 500%, compared to a reference. In other embodiments, the method decreases the level of a cytokine, chemokine, or protease, by at least 5%, 10%, 20%, more desirably by at least 25%, 30%, 35%, 40%, 50%, 60%, or even by as much as 70%, 80%, 90 or 100% compared to a reference. Methods for assaying the levels of biological compounds are routine, and are known to the skilled artisan (e.g., Guyton et al., Textbook of Medical Physiology, Tenth edition, W.B. Saunders Co., 2000).

Although not being bound to a particular theory, effects of elevated levels of cytokines, chemokines, and proteases in a pathology referenced herein result in local and systemic responses that consequently result in tissue damage. Tissue damage can lead to organ failure In preferred embodiments, the method increases the biological activity of the tissue or organ by at least 5%, 10%, 20%, 30%, 40%, 50%, 60%, 70%, 80%, 90%, 100%, 150%, or even by as much as 200%, 300%, 400%, or 500% compared to a corresponding, naturally-occurring tissue or organ. Biological functions of the tissue or organ amenable to assay include digestion, excretion of waste, secretion, electrical activity, muscle activity, hormone production, or other metabolic activity. Methods for assaying the biological activity of tissues and organs are routine, and are known to the skilled artisan (e.g., Guyton et al., Textbook of Medical Physiology, Tenth edition, W.B. Saunders Co., 2000).

Methods of the invention are useful for treating or stabilizing in a patient (e.g., a human or mammal) a condition, disease, or disorder affecting a tissue or organ. Therapeutic efficacy is optionally assayed by measuring, for example, the biological function of the treated tissue or organ (e.g., bladder, bone, brain, breast, cartilage, esophagus, fallopian tube, heart, pancreas, intestines, gallbladder, kidney, liver, lung, nervous tissue, ovaries, prostate, skeletal muscle, skin, spinal cord, spleen, stomach, testes, thymus, thyroid, trachea, ureter, urethra, urogenital tract, and uterus). Such methods are standard in the art. For example, bladder function is assayed by measuring urine retention and excretion. Brain, spinal cord, or nervous tissue function is assayed by measuring neural activity (e.g., electrical activity). Esophageal function is assayed by measuring the ability of the esophagus to convey food to the stomach. Heart function is assayed by electrocardiogram. Pancreatic function is assayed by measuring insulin production. Intestinal function is assayed by measuring the ability of intestinal contents to pass through to the bowel, and may be evaluated using a barium enema or gastrointestinal series. Gallbladder function is assayed using a gall bladder radionuclide scan. Kidney function is assayed by measuring creatinine levels, urine creatinine levels, or by clinical tests for creatinine clearance, or blood urea nitrogen. Liver function is assayed using liver function tests or a liver panel that measures liver enzyme levels, bilirubin levels, and albumin levels. Lung function is assayed using spirometry, lung volume, and diffusion capacity tests. Ovary function is assayed by measuring levels of ovarian hormones (e.g., follicle stimulating hormone). Prostate abnormality is assayed by measuring prostate specific antigen. Spleen function is assayed using a liver-spleen scan. Stomach function is assayed using a stomach acid test or by assaying gastric emptying. Testicular function is assayed by measuring levels of testicular hormones (e.g., testosterone). Other methods for assaying organ function are known to the skilled artisan and are described, for example, in the Textbook of Medical Physiology, Tenth edition, (Guyton et al., W.B. Saunders Co., 2000).

IαIp Compositions

As used herein, "IαIp composition" refers to a preparation of IαIp proteins, including IαI and PαI in physiological proportions. Physiological proportions, as used herein is intended to include proportions found in a person or animal that is not suffering from an infection or condition, and/or the ratio of IαI to PαI that appears naturally in human plasma. Physiological proportions are usually from between about 60% to about 80% IαI and between about 40% to about 20% PαI. Physiological proportions may vary from these ranges due to normal variations in genetic makeup of subjects.

As used herein, "IαIp complex" is intended to encompass all naturally occurring biologically active variants of the IαIp proteins, including proteins containing deletions, insertions, additions, and substitutions. A "natural variant" of an IαIp protein is defined as a peptide obtained from plasma having a sequence that is altered by one or more amino acids. The variant may have "conservative" changes, wherein a substituted amino acid has similar structural or chemical properties, e.g., replacement of leucine with isoleucine. In other embodiments, a variant may have "non-conservative" changes, e.g., replacement of a glycine with a tryptophan. Similar variations may also include amino acid deletions or insertions, or both. Guidance in determining which and how many amino acid residues may be substituted, inserted or deleted without abolishing biological or immunological activity may be found using computer programs well known in the art, for example, DNASTAR software. "Functionally equivalent" as used herein refers to any protein capable of exhibiting a substantially similar in vivo or in vitro activity as the IαIp proteins described herein, e.g., effecting a decrease in sepsis.

As used herein, "mixture of inter-alpha inhibitor protein (IαI) and pre-alpha protein (PαI)" refers to a composition containing both the IαI and PαI complexes. The mixture may also contain buffers, salts, or other components that are used to isolate the IαIp complex. In certain aspects, the IαI and the PαI are present in the mixture in a physiological proportion.

IαI and PαI present in the plasma fraction have an apparent molecular weight of between about 60 to about 280 kDa. Molecular weight may be determined by sodium dodecyl sulfate polyacrylamide gel electrophoresis.

The IαIp compositions of the invention may have a high trypsin inhibitory specific activity. The trypsin inhibitory specific activity of the IαIp compositions according to the invention may range from between about 100 to about 200 IU/mg. Preferably the trypsin inhibitory specific activity is above 120 IU/mg and even more preferably above 150 IU/mg. The trypsin inhibitory specific activity may be measured, for example, by the trypsin inhibitory assay using L-BAPA as a substrate. See, H U Bergmeyer, ed: vol 5, 3rd ed. 119 (1984) Verlag Chemie, Weinheim: Chromogenic substrate for the assay of trypsin: R. Geiger, H. Fritz, Methods of Enzymatic Analysis.

A composition of IαIp may be a mixture of inter-alpha inhibitor protein (IαI) and pre-alpha protein (PαI), wherein the IαI and the PαI are present in said mixture in a physiological proportion comprising a light chain of inter-alpha inhibitor protein associated with at least one of three heavy chains H1, H2 and H3. A composition according to the invention may also have a light chain of inter-alpha inhibitor protein associated with at least one of four heavy chains H1, H2, H3 and H4. Examples of each protein in the IαIp complex are as follows: Bikunin GenBank accession number: AAB84031, P02760; H1 GenBank accession number: P19827, NP—002206; H2 GenBank accession number: NP—002207, P19823; H3 GenBank accession number: NP—002208; H4 GenBank accession number: Q14624, NP—002209, which are each incorporated herein by reference in their entirety.

Purification of Inter-Alpha Inhibitor Protein (IαIp)

IαIp may be purified by chromatography. "Purifying," as used herein, refers to steps or processes of removing unwanted or contaminating proteins or components from a IαIp to produce a purified IαIp. For example, a plasma fraction containing IαI and PαI in physiological proportion may be run through at least one chromatography step to purify the IαIp. As used herein, "chromatography", may include liquid chromatogaphy or column chromatography. It is known in the art that chromatography has many descriptions and/or classifications which are not mutually exclusive. For example, liquid chromatography can be performed on a column. Column chromatography may include anion-exchange chromatography.

Typically, preparation of IαIp involves isolation of the sample and collection of fractions determined to contain the proteins of interest. Methods of isolation include, for example, solid phase extraction, chromatography, for example anion-exchange chromatography, size exclusion chromatography, ion exchange chromatography, heparin chromatography, affinity chromatography, sequential extraction, gel electrophoresis and liquid chromatography. Preparation may also include purifying, which may include the steps of chromatography, for example, ion exchange chromatography, heparin chromatography, affinity chromatography, sequential extraction, gel electrophoresis and liquid chromatography.

"Solid support" refers to a solid material which can be derivatized with, or otherwise attached to, a capture reagent. Exemplary solid supports include monolithic supports, particle-based supports, probes, and microtiter plates. As used herein, "monolithic supports" refers to a one-piece porous solid support. As used herein, "particle-based" supports refers to homogenous particles for packing a chromatography column, including chromatographic resins.

"Analyte" refers to any component of a sample that is desired to be detected. The term can refer to a single component or a plurality of components in the sample.

"Adsorption" refers to detectable non-covalent binding of an analyte to an adsorbent or capture reagent. An adsorbent surface refers to a surface to which is bound an adsorbent (also called a "capture reagent" or an "affinity reagent"). An adsorbent is any material capable of binding an analyte (e.g., a target polypeptide or nucleic acid).

A chromatographic adsorbent refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

A biospecific adsorbent refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents.

"Eluant" or "wash buffer" refers to an agent, typically a solution, which is used to affect or modify adsorption of an analyte to an adsorbent surface and/or remove unbound materials from the surface. The elution characteristics of a wash buffer or eluant can depend, for example, on pH, ionic strength, hydrophobicity, degree of chaotropism, detergent strength and temperature. In some embodiments of the invention, the purification method involves at least one buffer wash step. In the methods of the invention a buffer wash step involves applying a wash buffer having a low pH to the column (e.g., 4.0, 3.7, 3.5, 3.4, 3.3, 3.1, 2.9, 2.0). In one embodiment the low pH wash buffer has a pH less than about 4.0. In a preferred embodiment, the wash solution has a pH less than about 3.6. In an even more preferred embodiment, the wash solution has a pH less than about 3.3. Most preferably, the wash solution has a pH less than about 3.3 to about 2.9. In other embodiments, the purification method involves more than one buffer wash step. It is preferred that the subsequent buffer wash step has a lower pH than the preceding buffer wash step. In one embodiment, the first wash buffer has a pH of about 4.0 and the second wash buffer has a pH of about 3.6. In another embodiment, the first wash buffer has a pH of about 4.0 and the second wash buffer has a pH of about 3.1. In another embodiment, the first wash buffer has a pH of about 4.0 and the second wash buffer has a pH of about 2.9. In embodiments of the invention, the wash buffer is acetic acid or sodium acetate. Other wash buffers suitable for use in the invention include citric acid, glycine or phosphate buffer. In still other embodiments, the purification method involves a wash step with a salt containing buffer. It is preferred that the salt concentration in the salt containing buffer is higher than 250 mM NaCl (e.g., 260, 270, 280, 290 mM NaCl). In one embodiment, the first wash buffer has a salt concentration of 290 mM NaCl and the second wash buffer has a pH of about 2.9. It has been discovered that the addition of the salt wash step to the purification protocol involving a low pH step increases the yield and purity of the IαIp than when the salt wash step is absent. In embodiments of the invention, the salt in the salt containing wash buffer is sodium chloride (NaCl). Other salts suitable for use in the invention include potassium chloride (KCl).

Anion-exchange chromatography may be by monolithic support, for example, CIM with immobilized anion-exchange ligands such as DEAE-CIM or Q-CIM (BIA Separations). Anion-exchange chromatography may also be particle-based, for example, DEAE Sepharose, DEAE Sephadex A50, Toyopearl DEAE, TMAE Fractogel, DEAE Fractogel, or Q-Sepharose. SEPHAROSE is a trade name of Pharmacia, Inc. of New Jersey for a high molecular weight substance for the separation by gel filtration of macromolecules. Anion exchange columns have two components, a matrix and a ligand. The matrix can be, for example, cellulose, dextrans, agarose or polystyrene. The immobilized anion-exchange ligand can be diethylaminoethane (DEAE), polyethyleneimine (PEI), or a quaternary amine functional group (Q). The strength of an anion exchange column refers to the state of ionization of the ligand. Strong anionic exchange columns, such as, those, having a quaternary ammonium ligand, bear a permanent positive charge over a wide pH range. In weak anion exchange columns, such as DEAE and PEI, the existence of the positive charge depends on the pH of the column. Strong anion exchange columns such as Q Sepharose FF, or metal-chelating Sepharose (e.g., $Cu^{2+}$-chelating Sepharose) are preferred. Anion exchange columns are generally loaded with a low-salt buffer at a pH above the pI of the protein to be purified. The selection of buffers, buffer concentrations, salt concentrations, and eluents, are known to one skilled in the art (e.g., see Scopes "Protein Purification: Principles and Practice" Springer; 3rd ed. edition (Nov. 19, 1993))

In one embodiment of the invention, a sample can be purified by anion exchange chromatography. Anion exchange chromatography allows purification of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be further purified by heparin chromatography. Heparin chromatography allows further purification of the IαIp complexes in a sample also on the basis of affinity interaction with heparin and charge characteristics. Heparin, a sulfated mucopolysaccharide, will bind IαIp complexes with positively charged moieties and a sample can be sequentially eluted with eluants having different pH's or salt concentrations. IαIp complexes eluted with an eluant having a low pH are more likely to be weakly positively charged. IαIp complexes eluted with an eluant having a high pH are more likely to be strongly positively charged. Thus, heparin chromatography also reduces the complexity of a sample and separates IαIp complexes according to their binding characteristics. In another embodiment, a sample can be further purified by hydroxyapatite chromatography. In yet another embodiment, a sample can be further purified by hydrophobic interaction chromatography.

IαIp complexes may be may be captured with capture reagents immobilized to a support, such as any biochip, a multiwell microtiter plate, a resin, or nitrocellulose membranes that are subsequently probed for the presence of proteins. In particular, the IαIp complexes of this invention may be captured on Surface-Enhanced Laser Desorption/Ionization (SELDI) protein biochips. Capture can be on a chromatographic surface or a biospecific surface. Any of the SELDI protein biochips comprising reactive surfaces can be used to capture and detect the IαIp complexes of this invention. These biochips can be derivatized with the antibodies that specifically capture the IαIp complexes, or they can be derivatized with capture reagents, such as protein A or protein G that bind immunoglobulins. Then the IαIp complexes can be captured in solution using specific antibodies and the captured IαIp complexes isolated on chip through the capture reagent.

The purification of IαIp may be scaled according to volume and quantity. In some embodiments a 1 mL or 8 mL column is used to purify IαIp. In other embodiments for an 80 mL, 800 mL column, or 8 L column is used to purify IαIp.

Typically the purified IαIp is exchanged into a buffer to maintain the stability or activity after elution from the column. The purified IαIp may also be processed by ultrafiltration or diafiltration to remove low molecular weight protein contaminants. In some embodiments, viral inactivation steps are incorporated in the purification. Before the chromatographic separation, a solvent and detergent treatment of plasma may be used to inactivate virus particles. After ultrafiltration or diafiltration the purified IαIp may be further processed by nanofiltration (e.g., to inactivate viruses). Purified IαIp may also be lyophilized and packaged for long-term storage (stock piled).

The IαIp compositions of the invention are preferably from between about 85% to about 100% pure. As used herein, the term "pure" refers to the IαIp composition that is removed from its natural environment, isolated or separated, and is at least between about 85% to about 100% free, preferably 90% free, and more preferably 95% free from other components with which it is naturally associated. In preferred embodiments, a substantially purified protein will constitute more than 85%, 87.5%, 90%, 92.5%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. Any suitable materials and methods can be used to perform the isolation step or steps of blood plasma to obtain purified IαIp.

Various methods for quantifying the degree of purification of proteins, polypeptides, or peptides will be known to those of skill in the art in light of the present disclosure. These include, for example, determining the specific protein activity of a fraction or assessing the number of polypeptides within a fraction by gel electrophoresis. The term "biologically active" refers to having structural, regulatory or biochemical functions of a naturally occurring IαIp complex. Likewise, "immunologically active" defines the capability of the natural, recombinant or synthetic IαIp complex, or any oligopeptide thereof, to induce a specific immune response in appropriate animals or cells and to bind with specific antibodies. IαIp concentrations can be measured by a competitive Enzyme-Linked Immunosorbent Assay (ELISA) using MAb 69.31 as described in Lim et al, (J. of Infectious Diseases, 2003). In the competitive ELISA, antibodies which bind to the light chain of IαIp, e.g., MAb 69.26 and MAb 69.31 (Lim et al, J. of Infectious Diseases, 2003) may be used to detect whether the active site of IαIp is exposed. When using antibodies which bind to the light chain of IαIp in the competitive ELISA, a higher measurement obtained than would be predicted based on protein concentration may indicate that the active site of IαIp is exposed. The binding of anti-IαIp antibody to purified IαIp is increased by greater than 1-, 1.5-, 2-, 3-, 4-, 5-, or 10-fold, as determined by competitive ELISA. Methods for the measurement of protein concentration are known in the art and can also be measured by commercially available protein assays (Bicinchoninic acid (BCA) protein assays; BioRad protein assay). IαIp product structure and purity may be confirmed by, for example, HPLC or other chromatographic method known to one of skill in the art. Specific inhibitory activity of purified IαIp can be measured in a trypsin inhibition assay using the chromogenic substrate L-BAPA (N(alpha)-Benzoyl-L-arginine-4-nitroanilide hydrochloride (Fluka Chemicals). This assay is based on the ability of IαIp to inhibit the hydrolysis of L-BAPA. Inhibition can be monitored by a decrease in the rate of A absorbance/minute at 410 nm.

Purified IαIp has an apparent molecular weight of between about 60 to about 280 kDa. Molecular weight may be determined by sodium dodecyl sulfate polyacrylamide gel electrophoresis. The purified IαIp also has biological activity (e.g., cytokine inhibitor activity, chemokine inhibitor activity, or serine protease inhibitor activity) which can be determined by methods described herein or known in the art. Purified IαIp has at least as much biological activity compared to that of IαIp not treated with low pH, including, IαIp present in blood, plasma, or plasma fractions, or IαIp purified by other means.

The method also lends itself to the quantitation of inter-alpha inhibitor protein (IαIp) in a sample of unknown IαIp concentration. The sample of unknown IαIp concentration is applied to a chromatography column. In some embodiments, the volume of the chromatography column is less than 1 mL. The column to which the sample is applied is washed with a low pH buffer (e.g., pH less than 4.0). The column is subsequently eluted with a high salt buffer (e.g., >500 mM). The eluted protein, consisting substantially of IαIp (e.g., purity >90%), is measured by methods known in the art for determining protein concentration. Such methods may include UV absorbance, protein assays, or the competitive ELISA for determining IαIp concentration, as described herein. The amount of IαIp present in the sample may be obtained by comparing the quantity of the protein to one or more references. Such references include samples containing known quantities of IαIp that have been processed by the method used to process the sample of unknown IαIp concentration.

Blood, Plasma, and Plasma Fractions

Because IαIp is abundant in blood, IαIp is typically purified from blood, blood plasma, or a blood plasma fraction isolated from blood plasma. "Isolating," as used herein refers to producing a plasma fraction from blood plasma, which contains IaI and PαI in physiological proportions. For example, isolating a plasma fraction may be achieved in accordance with the invention by chromatographing blood plasma. Isolated refers to material removed from its original environment (e.g., the natural environment if it is naturally occurring), and thus is altered "by the hand of man" from its natural state. For example, an isolated polypeptide or protein could be a component of blood plasma, or could be contained within a cell and be considered "isolated" because that blood plasma or particular cell may not be the original environment of the polypeptide.

As used herein "blood plasma-derived" refers to being originally isolated or purified from blood plasma. That is, the natural environment of the composition is blood plasma.

As used herein, "a plasma fraction" is a fraction from an isolation or purification step, for example, chromatography, that was originally derived from blood plasma. Plasma fractions according to the invention may be for example, a side fraction obtained from the purification of clotting factor IX, a side fraction from the purification of a prothrombin complex concentrate, a cryosupematant resulting from cryoprecipitation (described in Hoffer et al., Journal of Chromatography B 669 (1995) 187-196) of blood plasma, or cryo-poor plasma. As used herein, "cryo-poor plasma" or "cryosupernatant" is the supernatant obtained from cryoprecipitation of plasma. Cryo-poor plasma may be prepared by thawing fresh frozen plasma (e.g., at 4 degree Celcius and centrifugation at 10 k rpm for 30 min).

Instead of plasma, this purification protocol can be used also on any plasma fraction containing IαIp. IαIp containing plasma fractions include side fractions or plasma intermediates during the industrial processing of clotting factors and other plasma derivatives or during the purification process of other therapeutic proteins such as clotting factors. An example of a side fraction according to the invention is one obtained from the purification of clotting factor IX. A mixture of IαI/PαI has been shown to be present in side-fractions generated during the purification of factor IX (FIX). The method of obtaining the side fraction obtained from the purification of clotting factor IX is described in Hoffer et al., Journal of Chromatography B 669 (1995) 187-196, which is hereby incorporated by reference in its entirety. Other examples of side fractions include side fractions from FIX purification or a side fraction from the purification of a prothrombin complex concentrate, as is described in D. Josic et al., Thrombosis Research 100 (2000) 433-441, which is hereby incorporated by reference in its entirety. Other examples of side fractions include side fractions from FIX purification designated herein as Fraction D and Fraction C. Fraction D and Fraction C refer to IαIp containing fractions obtained during the purification of FIX and other clotting factors, etc., by anion exchange chromatography. Fraction D is an IαIp containing fraction eluted from the anion exchange column under high salt conditions (e.g., >500 mM NaCl). Fraction C is an IαIp containing fraction which is derived from the a plasma fraction purified from an anion exchange column and eluted with 25 mM Citrate, pH 6.0, 0.5 M NaCl. Fraction C is the unbound fraction, i.e., the flowthrough, from an anti-Factor IX affinity purification step in which the eluant from the anion exchange column (in 25 mM Citrate, pH 6.0, 0.5 M NaCl) is applied to an anti-Factor IX affinity column.

An example of side fraction isolated as a cryosupernatant resulting from cryoprecipitation of blood plasma. For example, suitable cryoprecipitation methods are described in Hoffer et al., Journal of Chromatography B 669 (1995) 187-196.

Blood and blood plasma may be obtained from human, primate, bovine, equine, porcine, ovine, feline, or canine sources. The blood may be acquired and/or purchased from, for example, blood banks, hospitals, hospices, private companies, research foundations, or any other source of blood. The blood plasma may be acquired and/or purchased from, for example, blood banks, hospitals, hospices, private companies, research foundations, or any other source of blood. Alternately, blood plasma may also be isolated from blood once blood is obtained. Suitable methods of isolating blood plasma include gravity and centrifugation. Plasma fractions, according to the invention, may be from human, primate, bovine, equine, porcine, ovine, feline, or canine sources.

Some previous IαIp purifications from side fractions contained contamination by factor X (FX), which was detected by Western blot analysis as an 80 kDa band and in a clotting assay. The removal of FX is important because FX is thrombogenic and can be harmful if administered to humans. The methods of IαIp purification described herein remove FX contamination. Additionally, a solvent and detergent treatment of plasma before the chromatographic separation may be performed to inactivate any viruses present in the plasma or plasma fraction.

Therapeutic Methods

The invention provides for the treatment of diseases and disorders associated with a decrease in IαIp levels or an increase in the level of a chemokine, cytokine, or protease. Many diseases or conditions associated with a deficiency in cell number are characterized by an increase in the level of a chemokine, cytokine, or protease. Such diseases or pathological conditions include, but are not limited to, inflammation, trauma/injury, tumor invasion, tumor metastasis, sepsis, septic shock, or an infectious disease. Methods of the invention ameliorate such diseases, disorders, or injuries by decreasing the level or activity of a chemokine, cytokine, or protease.

The present invention provides methods of treating disease and/or disorders or symptoms thereof which comprise administering a therapeutically effective amount of a pharmaceutical composition comprising a purified IαIp protein herein to a subject (e.g., a mammal such as a human). Thus, one embodiment is a method of treating a subject suffering from or susceptible to a disease or disorder or symptom thereof characterized by a deficiency in IαIp. The method includes the step of administering to the mammal a therapeutic amount of an amount of a composition of the invention sufficient to treat the disease or disorder or symptom thereof; under conditions such that the disease or disorder is treated.

In various embodiments, agents of the invention are administered by local injection to a site of disease or injury, by sustained infusion, or by micro-injection under surgical conditions (Wolff et al., Science 247:1465, 1990). In other embodiments, the agents are administered systemically to a tissue or organ of a patient having a deficiency in IαIp.

The methods herein include administering to the subject (including a subject identified as in need of such treatment) an effective amount of purified IαIp protein described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. The subject may also be primate, bovine, equine, porcine, ovine, feline, or canine. Subjects suitable for treatment with IαIp may be identified as having inflammation, trauma/injury, tumor invasion, tumor metastasis, sepsis, septic shock, or an infectious disease. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The subject may be self-identified or diagnosed by a medical practitioner as having inflammation, tumor invasion, tumor metastasis, sepsis, septic shock, or an infectious disease. The subjects may be primates, humans, or other animals. The compositions herein may be also used in the treatment of any other disorders in which a deficiency in cell number may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with a deficiency in IαIp levels or an increase in chemokine, cytokine, or protease levels. The subject may have been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Compositions

The present invention features pharmaceutical preparations comprising agents capable of decreasing the levels of or inhibiting the activity of cytokines, chemokines, and proteases. Such preparations have both therapeutic and prophylactic applications. Agents useful in the methods described herein include those that decrease the level of a cytokine, chemokine, or protease. If desired, the compositions of the invention are formulated together with agents that decrease the levels of cytokines, chemokines, and proteases present in the circulation of a subject. Agents that decrease cytokine or chemokine response include, but are not limited to, anti-TNF-alpha antibody or TNF inhibitors.

Compounds of the invention may be administered as part of a pharmaceutical composition. The compositions should be sterile and contain a therapeutically effective amount of the agents of the invention in a unit of weight or volume suitable for administration to a subject. The compositions and combinations of the invention can be part of a pharmaceutical pack, where each of the compounds is present in individual dosage amounts.

Pharmaceutical compositions of the invention to be used for prophylactic or therapeutic administration should be sterile. Sterility is readily accomplished by filtration through sterile filtration membranes (e.g., 0.2 µm membranes), by gamma irradiation, or any other suitable means known to those skilled in the art. Therapeutic polypeptide compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

The compounds may be combined, optionally, with a pharmaceutically acceptable excipient. The term "pharmaceutically acceptable excipient" as used herein means one or more compatible solid or liquid filler, diluents or encapsulating substances that are suitable for administration into a human. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be also included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a disease or disorder characterized by a decrease in IαIp, an effective amount is sufficient to reduce the levels or activity of a chemokine, cytokine or protease; or sufficient to stabilize, slow, or reduce a symptom associated with a pathology. Compositions of the present invention may be used to treat acute inflammatory disease, sepsis, severe shock, septic shock, rheumatoid arthritis, cancer, cancer metastasis, infectious disease, or preterm labor can be straightforwardly determined. Generally, doses of the compounds of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Oral administration can be preferred for prophylactic treatment because of the convenience to the patient as well as the dosing schedule.

Pharmaceutical compositions of the invention can optionally further contain one or more additional proteins as desired. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian protein which has been introduced according to standard recombinant DNA techniques; or from the human biological fluids (e.g., blood, milk, lymph, urine or the like) or from transgenic animals that contain a gene that expresses a human protein which has been introduced according to standard transgenic techniques.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition. It is generally known to the skilled artisan that proteins and polypeptides are sensitive to changes in pH, temperature, and a multiplicity of other factors that may affect therapeutic efficacy.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyester-amides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly(2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 μm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3dioleyloxy)-propyl]-N, N, N-trimethylammonium chloride (DOTMA) and dimethyl dioctadecylammonium bromide (DDAB). Methods for making liposomes are well known in the art and have been described in many publications, for example, in DE 3,218, 121; Epstein et al., Proc. Natl. Acad. Sci. (USA) 82:3688-

3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Those of skill in the art will recognize that the best treatment regimens for using compounds of the present invention to treat acute inflammatory disease, sepsis, severe shock, septic shock, rheumatoid arthritis, cancer, cancer metastasis, infectious disease, or preterm labor can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained from the initial clinical trials and the needs of a particular patient.

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Combination Therapies

Compositions and methods of the invention may be administered in combination with any standard therapy known in the art. For example, the additional therapeutic agents may be anticancer agents, anti-inflammatory agents, anti-coagulants or immunomodulators. For example, dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (Pfizer), levamisol or thymosin, cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide. Anti-coagulants such as Anti-thrombin III, activated Protein C and protease inhibitors such as furin inhibitors.

If desired, an agent that induces tissue repair or regeneration or prevents cell death is administered together with an IαIp protein. Such agents include stem cells, collagens, fibronectins, laminins, integrins, angiogenic factors, anti-inflammatory factors, glycosaminoglycans, vitrogen, antibodies and fragments thereof, functional equivalents of these agents, and combinations thereof. Combinations of the invention may be administered concurrently or within a few hours, days, or weeks of one another. In one approach, an agent that induces tissue repair or regeneration or prevents cell death is administered prior to, concurrently with, or following administration of a conventional therapeutic described herein.

Kits

The invention provides kits for the purification of an IαIp protein. In one embodiment, the kit includes reagents for the chromatographic purification of IαIp protein. In some embodiments, the kit comprises a sterile container which contains a low pH wash buffer (e.g., pH 3.1-4.0); such containers can be ampules, bottles, vials, tubes, bags, pouches, blister-packs, or other suitable container forms known in the art. Such containers can be made of plastic, glass, or other materials suitable for holding reagents.

If desired a kit of the invention provides reagents for the purification of IαIp protein together with instructions for the purification protocol. The instructions will generally include information about the buffer conditions and volumes used in the purification protocol. In other embodiments, the instructions include at least one of the following: description of the reagents or combination of reagents; precautions; warnings; scientific studies; and/or references. The instructions may be printed directly as a separate sheet, pamphlet, card, or folder or on a container (when present) or label applied to a container supplied in or with the kit.

The invention provides kits for the increase of inter-alpha inhibitor protein (IαIp) levels in a subject or the decrease of cytokine, chemokine, or protease levels in a subject. The invention also provides kits for the treatment or prevention of a disease, disorder, or symptoms thereof associated with the decrease of IαIp levels in a subject or the increase of cytokine, chemokine, or protease levels in a subject. Diseases, disorders, or symptoms thereof may include acute inflammatory disease, sepsis, severe shock, septic shock, rheumatoid arthritis, cancer, cancer metastasis, trauma/injury, infectious disease, or preterm labor. In one embodiment, the kit includes a pharmaceutical pack comprising an effective amount of purified IαIp. Preferably, the compositions are present in unit dosage form. In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject in need thereof. The instructions will generally include information about the use of the compounds for the treatment or prevention of a disease or disorder amenable to treatment with IαIp (e.g., acute inflammatory disease, sepsis, severe shock, septic shock, rheumatoid arthritis, cancer, cancer metastasis, trauma/injury, infectious disease, or preterm labor). In other embodiments, the instructions include at least one of the following: description of the compound or combination of compounds; dosage schedule and administration for increasing IαIp levels in a subject, and/or decreasing cytokine, chemokine, or protease levels in a subject; dosage schedule and administration for treatment of acute inflammatory disease, sepsis, severe shock, septic shock, rheumatoid arthritis, cancer, cancer metastasis, trauma/injury, infectious disease, or preterm labor or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention also provides kits for the analysis of inter-alpha inhibitor protein (IαIp) in a sample. In one embodiment, the kit includes a known amount of purified IαIp. The known amount of purified IαIp may be used as an analytical reference for the measurement of of IαIp in a sample of unknown IαIp concentration. Preferably, the compositions are present in aliquots. In some embodiments, the kit comprises a sterile container which contains an aliquot of the purified IαIp; such containers can be boxes, ampoules, bottles, vials, tubes, bags, pouches, blister-packs, or other suitable container forms known in the art. Such containers can be made of plastic, glass, laminated paper, metal foil, or other materials suitable for holding compounds or solutions. In other embodiments, the instructions include at least one of the following: description of the compound or combination of compounds. The instructions may be printed directly on the container (when present), or as a label applied to the container, or as a separate sheet, pamphlet, card, or folder supplied in or with the container.

EXAMPLES

Example 1. IαIp was Purified in a Single Chromatographic Step that Involves Washing with Low pH Buffer A scheme for the purification of IαIp from human plasma using a single chromatographic step involves a low pH wash (FIG. 1A). The IαIp purification protocol with a low pH wash step was used to purify IαIp from cryo-poor plasma. Cryo-poor plasma (1:10 dilution in 25 mM Tris+200 mM NaCl, pH 7.6; 0.2 μM filtered). Diluted plasma (fifty (50) column volumes) was applied to a commercially available 1 mL DEAE monolithic column (DEAE-CIM; BIA Separations) at a flow rate of 5 column volumes (cv) per minute. The binding capacity of the column was predicted to be about 50 mL diluted plasma per 1 mL column volume. The flowthrough was collected. Additional plasma dilution buffer (20 column volumes 25 mM Tris, 200 mM NaCl, pH 7.6) was applied to the column to allow the starting material to pass through the column completely. When the flowthrough peak returned to baseline, the column was washed with wash buffer (5 column volumes of 150 mM Acetic acid, pH 4.0, or 200 mM Acetic acid, pH 3.3) and the peak was collected. After the low pH wash, the column was further washed with a buffer to increase the pH to that prior to the low pH wash (15 column volumes 100 mM Tris, 100 mM NaCl, pH 7.6) in preparation for the elution. The bound protein was eluted with a high salt elution buffer (15 column volumes 25 mM Tris, 1000 mM NaCl, pH 7.6). The peak was collected and this fraction contained highly pure IαIp. To exchange buffer and remove low molecular weight solutes and salts, ultrafiltration or diafiltration was performed using a membrane cut off of 30 kDa. The purified IαIp can also be lyophilized.

Figure 2A:
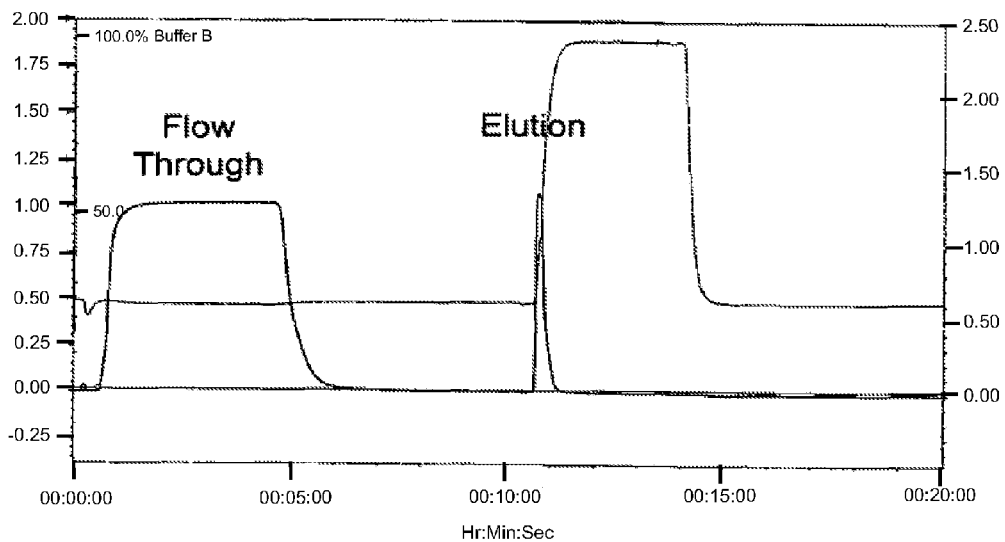
FIGS. 2A-2C show the purification of IαIp protein from plasma (Fraction D and Fraction C) by DEAE chromatography using a low pH wash step (pH 4.0 or pH 3.3).
Figure 2B:
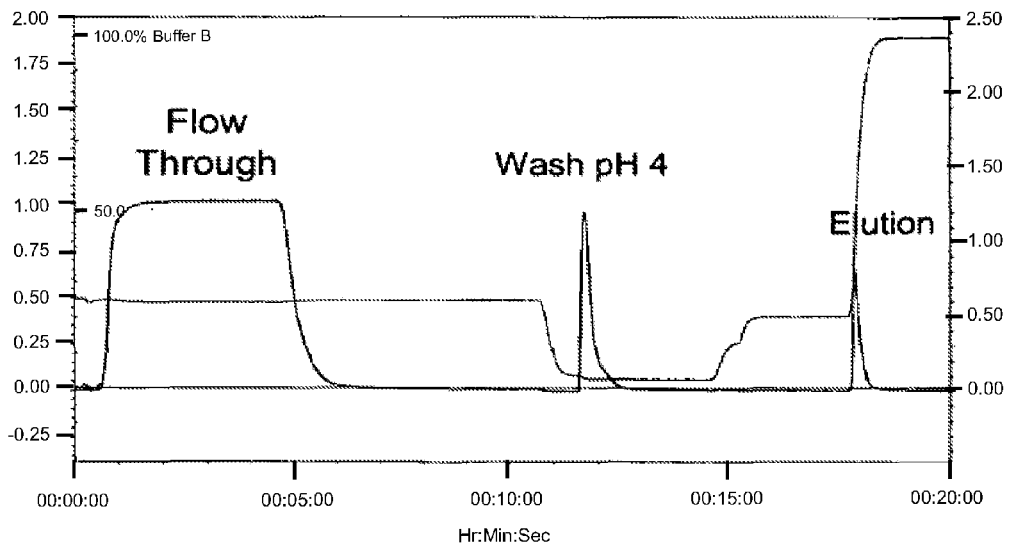
Figure 2C:
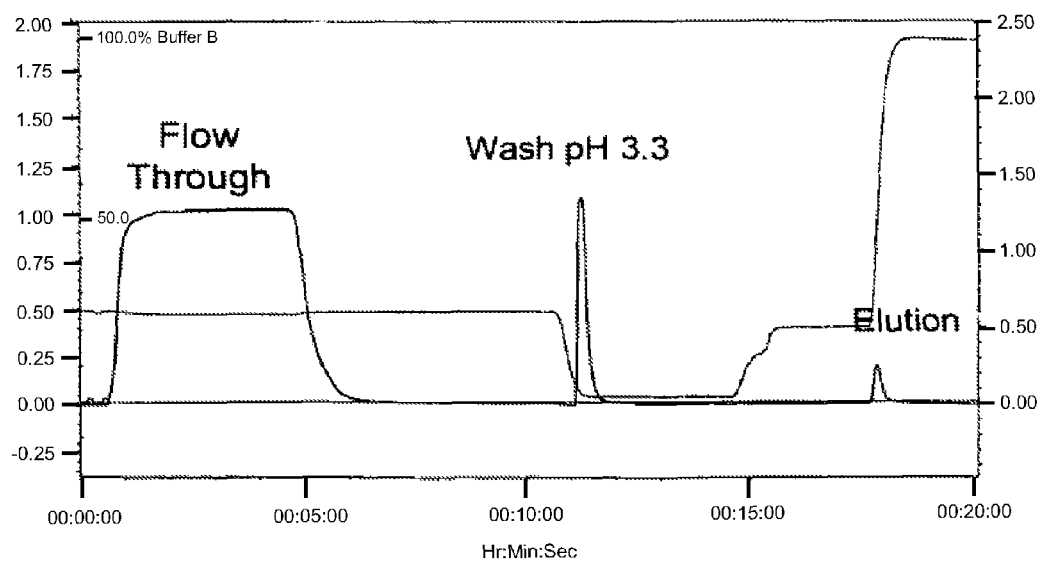

Fractionation of identical amounts of plasma by DEAE monolithic chromatography using three different wash buffers in three individual separations was used to determine the effect of lowering the pH during the wash step on the purification of IαIp protein. Fractionation of plasma by DEAE monolithic chromatography without using a low pH wash (pH 7.6) resulted in the elution of a relatively large peak when eluted with 1000 mM NaCl (pH 7.6) (FIG. 2A). The purified IαIp had a yield greater than 95% IαIp with a purity between about 10-15%. Applying a low pH wash (pH 4.0) resulted in a large peak representing the separation of further contaminants by the low pH wash before elution with 1000 mM NaCl (pH 7.6). In the eluted fraction about 95% IαIp was recovered with 40-50% purity (FIG. 2B). Lowering the pH of the wash step to pH 3.3 resulted in a reduction in the size of elution peak compared to that at pH 4.0 (FIG. 2C). The yield from the elution was about 90% IαIp at a purity of 80-90% (FIG. 2C). These studies show that lowering the pH during the wash step results in higher purity of IαIp with minimal reduction in the yield.

Figure 3:
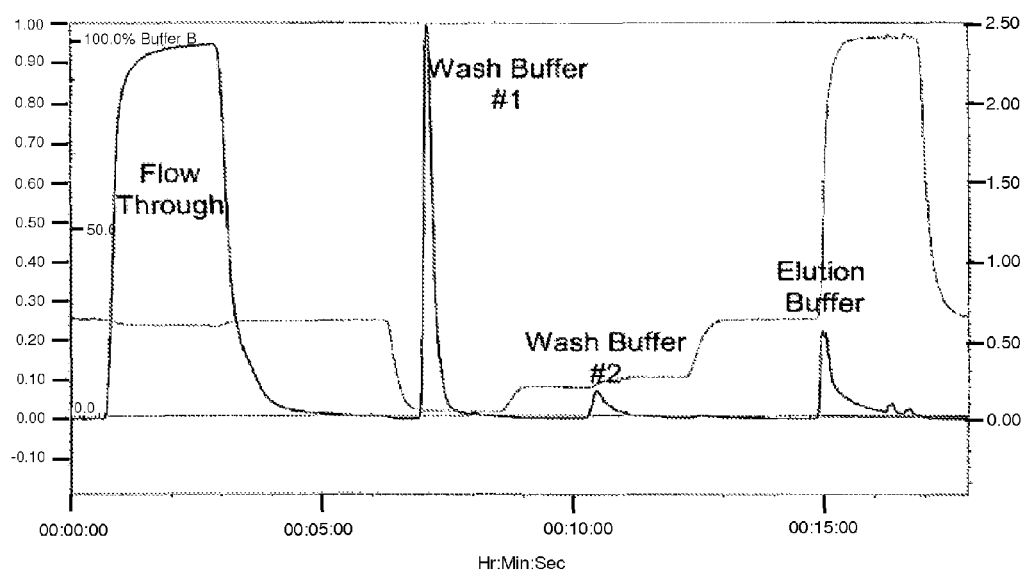
FIG. 3 shows a UV trace of cryo-poor plasma (1 mL of 1:100 dilution in 25 mM Tris, 200 mM NaCl, pH 7.8) separated by DEAE chromatography (monolithic support) with two wash steps using two low pH wash buffers (Wash Buffer #1: 150 mM Acetic Acid, pH 4.0; Wash Buffer #2: 200 mM Acetic Acid, pH 3.3) and eluted with 100 mM Tris+1000 mM NaCl, pH 7.6.
Figure 4A:
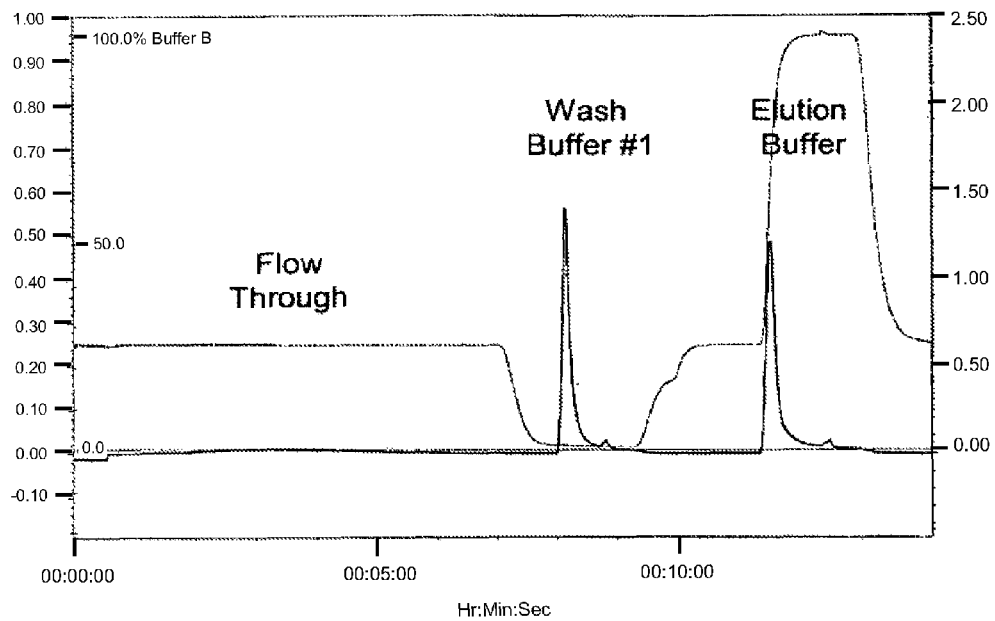
FIGS. 4A-4D show the fractionation of intermediate plasma (Fraction D and Fraction C) by DEAE chromatography using a single low pH wash step (pH 3.3) or two low pH wash steps (pH 4.0 and pH 3.3).
Figure 4B:
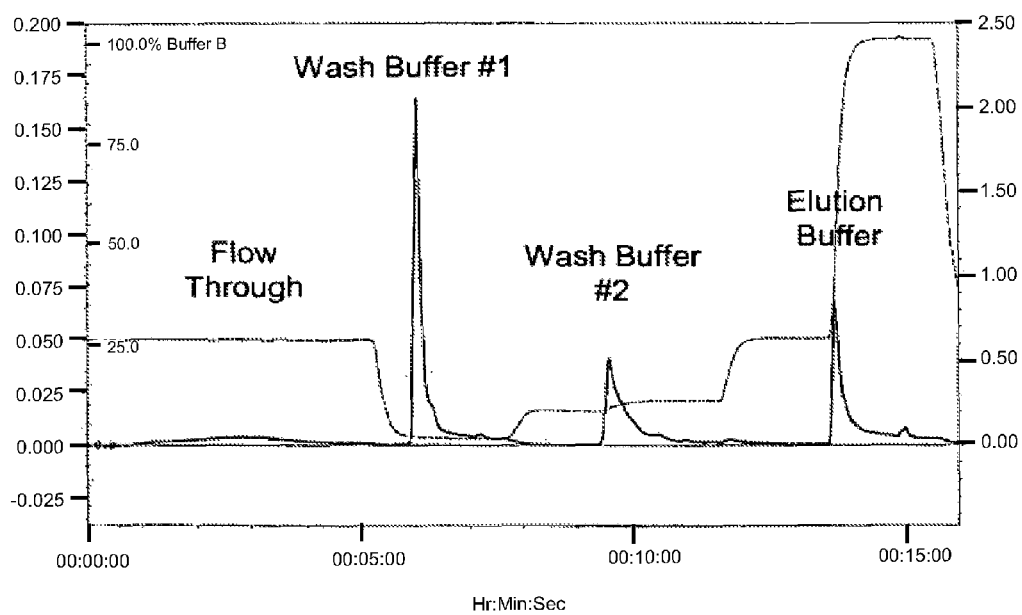
Figure 4C:
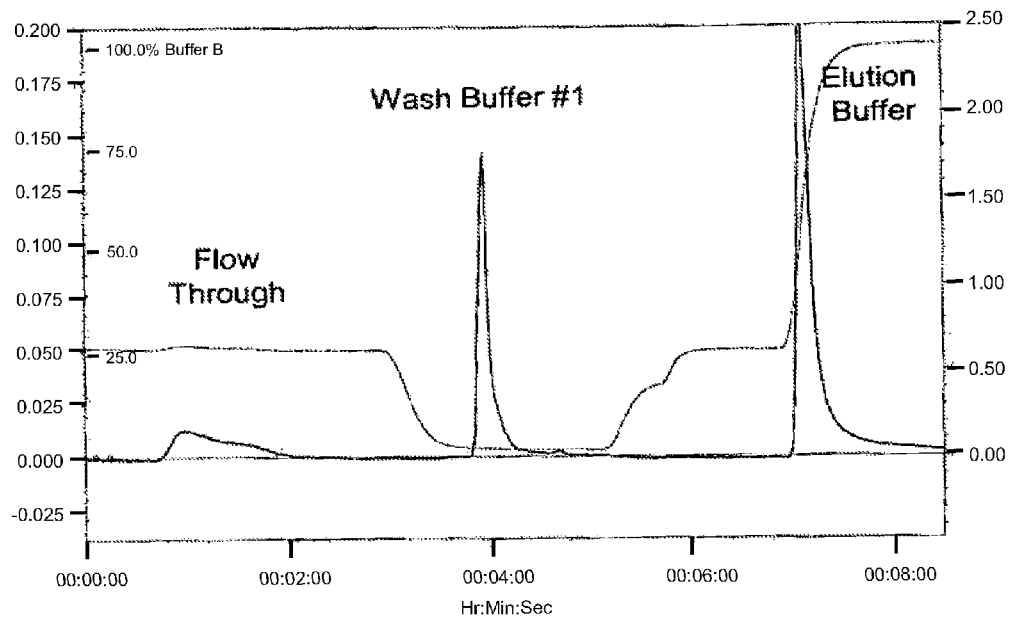
Figure 4D:
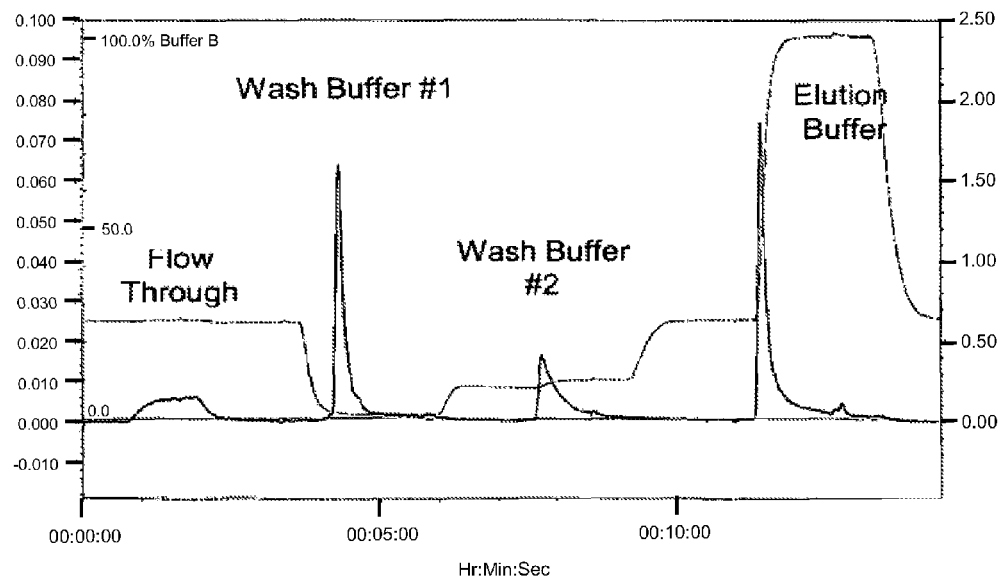

Cryo-poor plasma was separated by DEAE monolithic chromatography using two low pH wash buffers (150 mM Acetic Acid, pH 4.0, and 200 mM Acetic Acid, pH 3.3) was used to examine the effect on the fractionation of the proteins (FIG. 3). Each low pH wash resulted in the removal of a quantity of protein from the column. Because two peaks were observed corresponding to the application of the two low pH wash buffers, this result suggested that a second low pH wash at pH 3.3 could further remove contaminants that were not removed by the first low pH wash at pH 4.0. Similar results showing the removal of further proteins by a second low pH wash step were observed when Fraction D and Fraction C were used as starting material (FIGS. 4A-4D).

Figure 5:
FIG. 5 shows the purification of IαIp protein by DEAE monolithic column chromatography as analyzed by Western blot. Analysis of two chromatographic separations from intermediate plasma fractions (Fraction D and Fraction C) are shown. For each chromatographic separation, equivalent amounts were loaded per lane of the Starting material (SM), the Wash #1 fraction (W#1), the Wash #2 fraction (W#2), and Eluate (E)) were separated by SDS-PAGE (6%; non-denaturing). The Eluate (E) from a chromatographic separation of cryo-poor plasma is shown for comparison. The SDS-PAGE separated proteins were transferred to nitrocellulose membrane, which was probed with anti-human IαIp (MAb 69.26) as the primary antibody.

Fractions from the purification of IαIp protein from Fraction D starting material by DEAE monolithic column chromatography was also analyzed by Western blot (FIG. 5). In the first low pH wash (150 mM Acetic Acid, pH 4.0) IαIp (250 kDa) could be detected. In the second low pH wash (200 mM Acetic Acid, pH 3.3), some IαIp (250 kDa and 125 kDa) also became unbound from the column and eluted in the did not bind. However the predominant amount of IαIp protein purified was detected in the eluate. Similar results were observed for the purification of IαIp protein from Fraction C starting material by DEAE monolithic column chromatography using two low pH washes.

Quantitation of the yield and purity was also determined for fractions from separation of Fraction D starting material by DEAE monolithic column chromatography (DEAE-CIM; BIA Separations) using two low pH wash steps (pH 4.0 and pH 3.3) (Table 1).

TABLE 1

| | Total Protein (mg) | Total IαIp (mg) | % of IαIp (purity) | % of Total IαIp (Yield) |
|---|---|---|---|---|
| Starting Material | 48.0 | 13.6 | 26% | — |
| Flowthrough | 3.1 | 0.1 | 0.05% | 0.007% |
| Wash #1 (pH 4.0) | 24.1 | 0.6 | 0.07% | 4.4% |
| Wash #2 (pH 3.3) | 9.1 | 2.1 | 25% | 15% |
| Elution | 11.5 | 10.4 | 90% | 76% |

Analysis of the fractions indicated that greater that >99% of the IαIp in the starting material bound the column at 25 mM Tris, 200 mM NaCl, pH 7.6, as about 0.007% of the total IαIp was detected in the flowthrough. Applying a first wash step (150 mM Acetic Acid, pH 4.0) to the column resulted in the elimination of a large quantity contaminants (~50% total protein) with some loss of IαIp (4.4% total IαIp). Applying a second wash step (200 mM Acetic Acid, pH 3.3) to the column resulted in the further elimination of a large quantity contaminants (~19% total protein) with acceptable loss of IαIp (15% total IαIp). Elution of the remaining bound protein with high salt (25 mM Tris+1000 mM NaCl, pH 7.6), yielded 76% of total IαIp that was 90% pure. Analysis of the fractions correlated with the Western blot analysis of similar fractions (FIG. 5). This analysis shows that IαIp was substantially purified in a single chromatographic step by washing with low pH buffer.

Figure 6A:
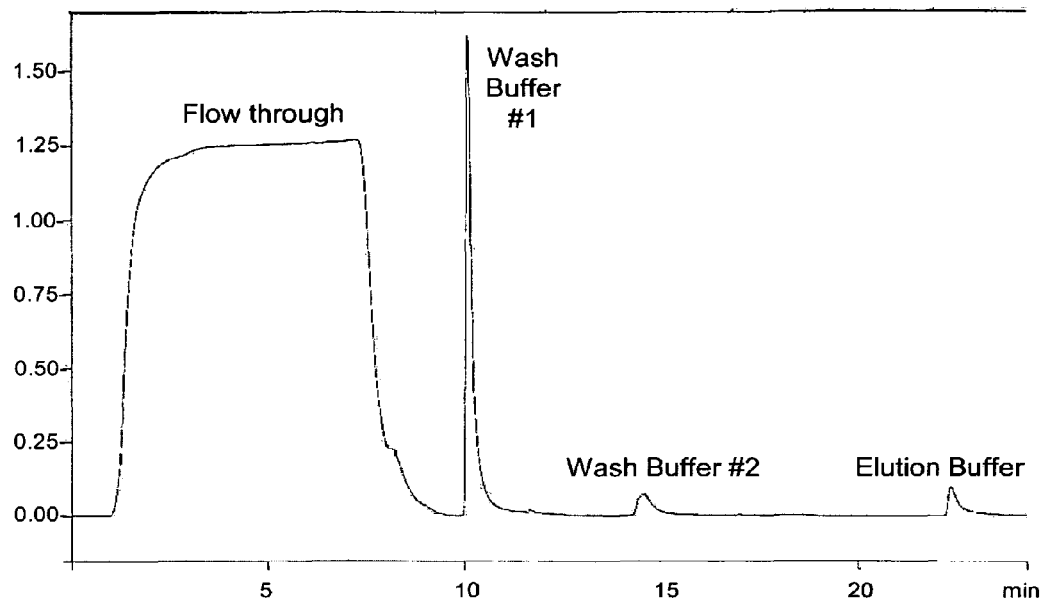
Figure 6B:
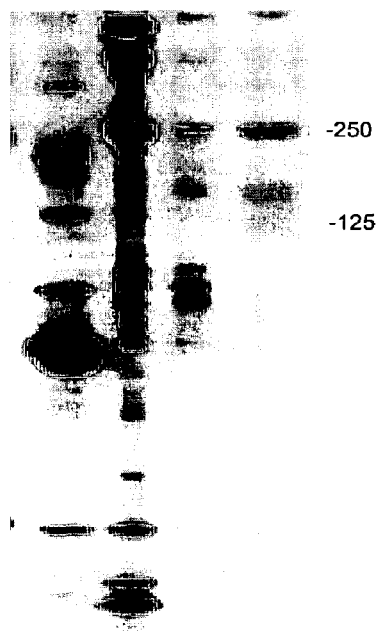
Figure 6C:
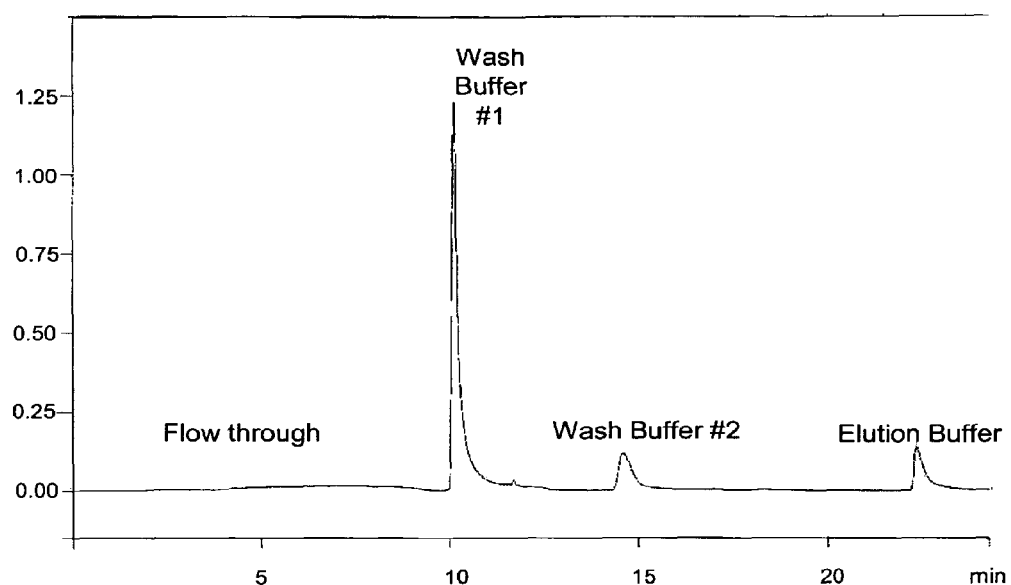
Figure 6D:
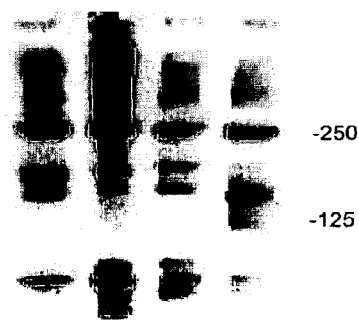
Figure 6E:
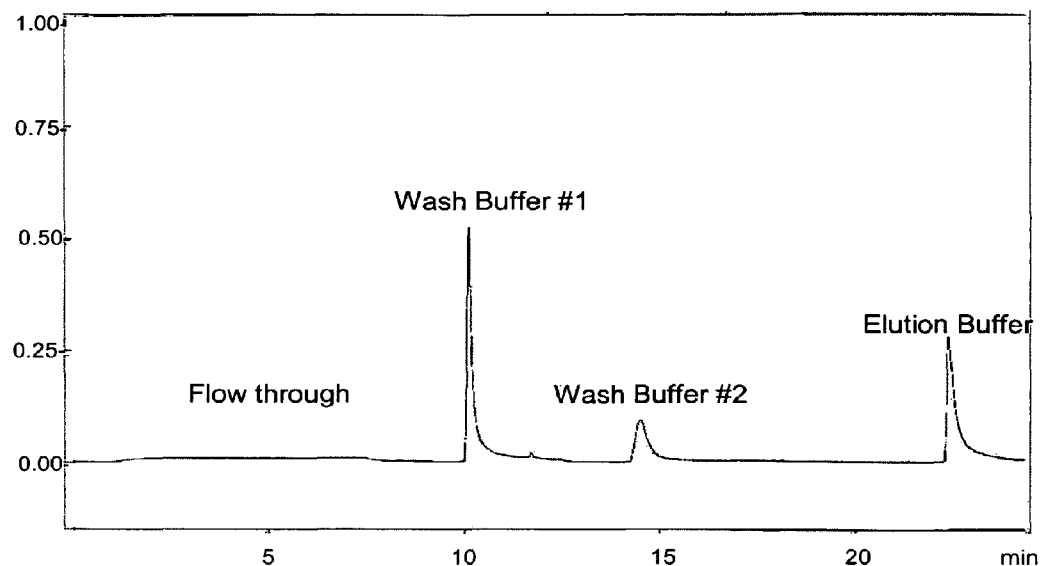
Figure 6E:
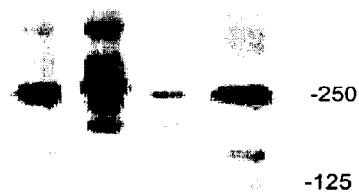

Example 2. Chromatographic Purification of IαIp Protein with a Low pH Wash Step can be Scaled Up To determine whether the IαIp purification protocol with the low pH wash step could be scaled up to a larger column volume, chromatography of cryo-poor plasma and intermediate plasma fractions (Fraction D and Fraction C) was performed on an 8 ml DEAE monolithic column. UV were similar to cryo-poor plasma and intermediate plasma fractions separated on the 1 ml DEAE monolithic column. (FIGS. 6A, 6C, and 6E). Fractions from each chromatographic separation were also analyzed by non-denaturing SDS-PAGE (FIGS. 6B, 6D, and 6F). Eluted fractions for the purification of the various starting materials showed the presence of 250 kDa and 125 kDa bands, which correspond to the molecular weights of IαIp protein. Thus the IαIp purification could be scaled up 8-fold to a larger column volume. The results suggest that IαIp protein can be purified with the low pH wash method on a larger scale (e.g., 800 mL column and 8 L column).

Example 3. IαIp Protein Purified with a Low pH Wash Step Showed Increased Binding of Antibody to Human IαIp in a Competitive ELISA Assay To determine the quantity and quality of IαIp purified on DEAE monolithic column chromatography with a low pH wash compared to that without, IαIp concentrations purified under both conditions was analyzed by a competitive Enzyme-Linked Immunosorbent Assay (ELISA) using MAb 69.31 as described by Lim et al. (J. of Infectious Diseases, 2003). The purified fraction was also quantitatively measured by a commercially available bicinchoninic acid (BCA) protein assay to determine total protein concentration. Surprisingly, the IαIp concentration measured by competitive ELISA was higher than even the total protein concentration measured by BCA protein assay for IαIp purified using a wash condition of pH 3.3. The IαIp purified using the low pH wash was observed in the competitive ELISA to have a concentration 300% higher than predicted, when compared to either an equivalent amount of the starting material loaded on the column or an equivalent amount of IαIp purified without using a low pH wash condition. Increased apparent IαIp concentration in the competitive ELISA was also observed for IαIp purified using low pH wash conditions of pH 3.6 and 3.3 but was not observed for IαIp purified using a wash condition of pH 4.0.

Because the total protein remained constant in the samples assayed in the competitive ELISA, this result suggested that some alteration, or even activation, might be triggered during the purification. Without being bound to any particular theory, it is believed that the active site of IαIp is exposed by conditions of low pH. The MAb 69.31 antibody used in the competitive ELISA recognizes an epitope that is located in the active site of the molecules. If the active site were exposed, the concentration from the competitive ELISA would apparently increase for IαIp purified under low pH conditions, when controlling for the amount of protein being measured. Thus low pH conditions may block the inhibitory activity of IαIp, thereby increasing the activity.

To determine whether the inhibitory activity of IαIp was altered by low pH conditions, the biological activity of IαIp was measured in a trypsin inhibition assay using the chromogenic substrate L-BAPA (N(alpha)-Benzoyl-L-arginine-4-nitroanilide hydrochloride, Fluka Chemicals). This assay measures specific inhibitory activity based on the ability of IαIp to inhibit the hydrolysis of L-BAPA. Inhibition can be monitored by a decrease in the rate of Δ absorbance/minute at 410 nm. Specific inhibitory activity of IαIp purified with low pH wash was calculated and compared to that of IαIp purified without a low pH wash. Low pH conditions during chromatography (i.e., pH above about 3.3) did not inactivate or lower the biological activity of the purified IαIp, compared to IαIp purified without using low pH. These results show that IαIp purified with a low pH wash step is at least as biologically active as that purified without using low pH conditions.

Figure 7A:
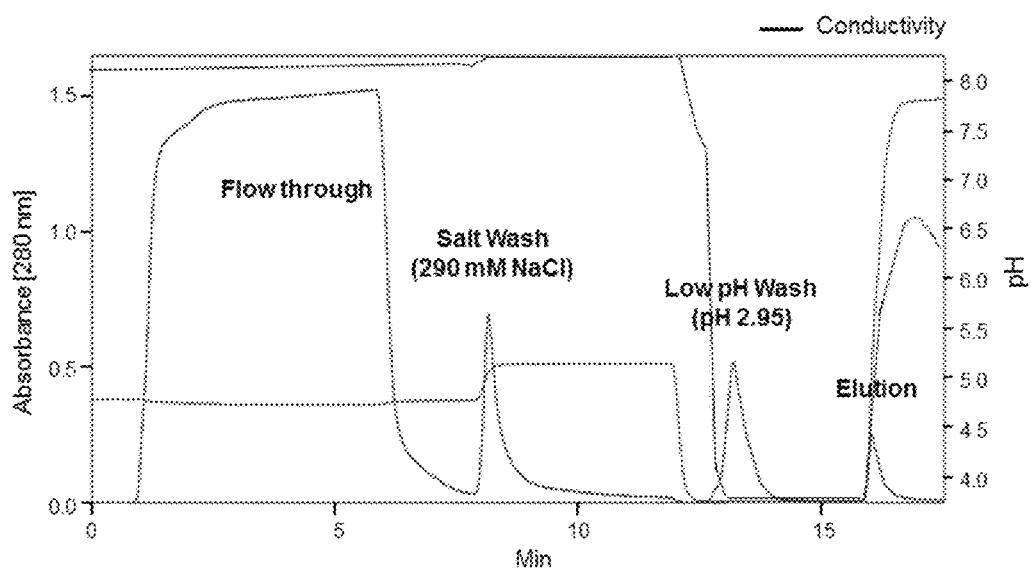
FIGS. 7A and 7B show the purification of IαIp protein from cryo-poor plasma or intermediate plasma fraction by DEAE chromatography using a wash step with a salt buffer (greater than 250 mM NaCl) and a low pH wash step (pH 2.95).

Example 4. IαIp was Purified in a Single Chromatographic Step that Involves Washing with a Buffer Containing Salt and with a Low pH Buffer A scheme for the purification of IαIp from human plasma using a single chromatographic step involves a salt buffer wash step and a low pH wash step (FIG. 1B). The IαIp purification protocol with a salt buffer wash step and a low pH wash step was used to purify IαIp from cryo-poor plasma (FIG. 7A). Cryo-poor plasma (12.5 column volumes of 1:10 dilution in 40 mM Tris+200 mM NaCl, pH 7.6; 0.2 μM filtered). Diluted plasma was applied to a commercially available 8 mL DEAE monolithic column (DEAE-CIM; BIA Separations) at a flow rate of 2.5 column volumes (cv) per minute. The flowthrough was collected. Additional loading buffer (7 column volumes of 25 mM Tris, 200 mM NaCl, pH 7.6) was applied to the column to allow the starting material to pass through the column completely. When the flowthrough peak returned to baseline, the column was washed with salt containing wash buffer (10 column volumes of 40 mM Tris-HCl, 290 mM NaCl, pH 7.6) and the peak was collected. After the salt wash, the column was additionally washed with a low pH buffer (10 column volumes of 200 mM Na-Acetate, pH 2.95) and the peak was collected. Following the second wash, the bound protein was eluted with high salt elution buffer (5 column volumes 40 mM Na-Citrate pH 6.50, 1000 mM NaCl). The peak was collected and this fraction contained highly pure IαIp.

Figure 7B:
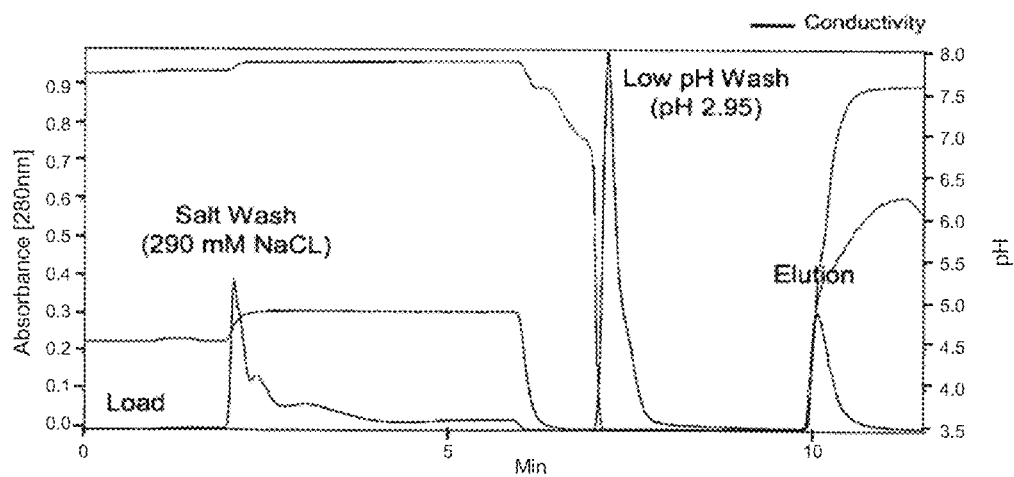

The IαIp purification protocol with a salt buffer wash step and a low pH wash step was used to purify IαIp from intermediate plasma fraction (Fraction D) (FIG. 7B). Intermediate plasma fraction (2.5 column volumes, 1:10 dilution in 40 mM Tris+200 mM NaCl, pH 7.6; 0.2 μM filtered) was applied to a commercially available 8 mL DEAE monolithic column (DEAE-CIM; BIA Separations) at a flow rate of 2.5 column volumes (cv) per minute. The flowthrough was collected. Loading buffer was applied to the column to allow the starting material to pass through the column completely. When the flowthrough peak returned to baseline, the column was washed with salt containing wash buffer (10 column volumes of 40 mM Tris-HCl, 290 mM NaCl, pH 7.6) and the peak was collected. After the salt wash, the column was additionally washed with a low pH buffer (10 column volumes of 200 mM Na-Acetate, pH 2.95) and the peak was collected. Following the second wash, the bound protein was eluted with high salt elution buffer (5 column volumes 40 mM Na-Citrate pH 6.50, 1000 mM NaCl). The peak was collected and this fraction contained highly pure IαIp.

Quantitation of the yield and purity was also determined for fractions from separation of Fraction D starting material by DEAE monolithic column chromatography (DEAE-CIM; BIA Separations) using a salt containing buffer wash step (290 mM NaCl) and a low pH wash step (pH 2.95) (Table 2).

TABLE 2

| | Total Protein (mg) | Total IαIp (mg) | % of IαIp (purity) | % of Total IαIp (Yield) |
|---|---|---|---|---|
| Starting Material | 28.7 | 5.6 | 19.5% | — |
| Flowthrough | 0.2 | n.d. | n.d. | — |
| Salt Buffer Wash | 9.0 | 0.38 | 4.2% | 6.8% |
| Low pH Wash (pH 2.95) | 14.1 | 0.28 | 2.0% | 5.0% |
| Elution | 5.4 | 5.0 | 91.8% | 88.2% |

(n.d = not detectable)

This analysis shows that addition of a salt buffer wash step to a purification protocol involving a low pH buffer wash step yields 88.2% IαIp purified from a plasma fraction. In comparison to the results of Table 1, the addition of a salt buffer wash step to a purification protocol involving a low pH buffer wash step increases the yield of IαIp purified from plasma or a plasma fraction.

Figure 8:
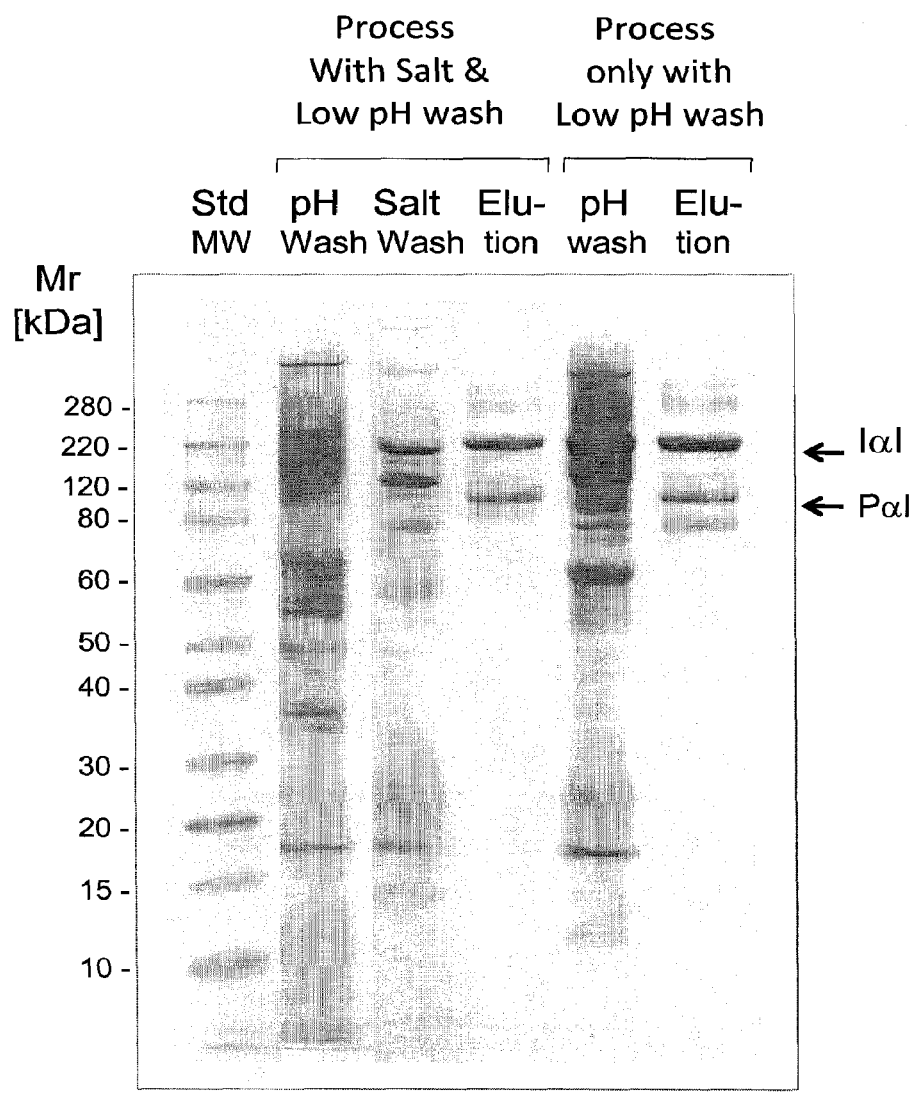
FIG. 8 shows SDS-PAGE analysis of fractions from the purification of IαIp protein including a salt wash step (290 mM NaCl) and a low pH wash step (pH 2.95) compared to fractions from the purification of IαIp protein using a low pH wash step (pH 2.95). Fractions were eluted by Wash buffer pH 2.95 (pH wash), Wash buffer containing 290 mM NaCl (Salt wash), and Elution buffer containing 1000 mM NaCl (Elution) and separated by SDS-PAGE (4-12% gradient; non-denaturing). In both chromatographic procedures, IαIp protein was purified from intermediate plasma fraction (Fraction D). Standard Molecular Weight Proteins (Std MW) were run for comparison. Arrows—250 kDa Inter-alpha Inhibitor and 125 kDa Pre-alpha Inhibitor.

Additionally, SDS-PAGE analysis of the fractions of the two methods showed the presence of a ~75-80 kDa band present in the eluted fraction when a low pH wash step (pH 2.95) was performed, but not when a salt wash step (290 mM NaCl) and a low pH step (pH 2.95) were both performed (FIG. 8). The eluted fraction of the IαIp purification protocol with a salt wash step and a low pH step consisted substantially of two protein bands corresponding to inter-alpha inhibitor (250 kDa) and pre-alpha inhibitor (125 kDa). Thus the eluted fraction contained highly pure IαIp when the purification protocol involved a salt wash step and a low pH step.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition comprising 85% to 100% inter-alpha inhibitor proteins (IαIps) by weight, wherein the composition is suitable for administration to a human, and wherein the IαIps are characterized as having increased binding to an anti-IαIp antibody selected from the group consisting of MAb 69.26 and MAb 69.31 in a competitive Enzyme-Linked Immunosorbent Assay (ELISA) compared to IαIps not exposed to a wash buffer having a pH of 4.0 or lower.

2. A pharmaceutical composition comprising the composition of claim 1 and a pharmaceutically acceptable excipient.

3. A method for treating disease or disease symptoms in a subject, wherein the disease is selected from the group consisting of sepsis, severe shock, septic shock, and trauma/injury, comprising administering to the subject the composition of claim 1.

4. The method of claim 3, wherein the subject is identified as in need of treatment with a composition comprising IαIps.

5. A kit comprising the composition of claim 1 and instructions for therapeutic use or analytical use.

6. The composition of claim 1, wherein the labs IαIps exhibit increased binding in the competitive ELISA of greater than 1-, 1.5-, 2-, 3-, 4-, 5-, or 10-fold compared to the IαIps not exposed to a wash buffer having a pH of 4.0 or lower.

7. The composition of claim 1, wherein the IαIps are from blood, blood plasma, or a blood plasma fraction.

8. The composition of claim 1, wherein the IαIps have an apparent molecular weight of between about 60 to about 280 kDa.

9. The composition of claim 1, wherein the IαIps have biological activity.

10. The composition of claim 9, wherein the biological activity is a cytokine inhibitor activity, chemokine inhibitor activity, or a serine protease inhibitor activity.

11. The composition of claim 1, wherein the IαIps comprise inter-alpha inhibitor (Iap and pre-alpha inhibitor (PαI) in physiological proportions.

12. The composition of claim 11, wherein the IαI comprises between about 60% to about 80% of the IαIps in the composition and/or wherein the PαI comprises between about 20% to about 40% of the IαIps in the composition.

13. The composition of claim 1, wherein the composition is formulated to provide a dose of the IαIps to a subject of 1 mg/kg body weight to 5,000 mg/kg body weight.

14. The composition of claim 13, wherein the composition is formulated to provide a dose of the IαIps to a subject of 1 mg/kg body weight to 10 mg/kg body weight.

15. The composition of claim 14, wherein the subject is a human.

16. The composition of claim 1, further comprising a pharmaceutically acceptable excipient.

17. The composition of claim 16, wherein the composition is formulated for oral, rectal, topical, intraocular, buccal, intravaginal, intracisternal, intracerebroventricular, intrathecal, nasal, transdermal, subcutaneous, intramuscular, or intraperitoneal administration, for infusion, or for application within or onto an implant.

18. The composition of claim 17, wherein the composition further comprises cellulose.

* * * * *

UNITED STATES PATENT AND TRADEMARK OFFICE
CERTIFICATE OF CORRECTION

PATENT NO. : 9,758,570 B2
APPLICATION NO. : 14/859705
DATED : September 12, 2017
INVENTOR(S) : Yow-Pin Lim et al.

It is certified that error appears in the above-identified patent and that said Letters Patent is hereby corrected as shown below:

In the Claims

Column 32, Line 9, replace "the labs IαIps" with --the IαIps--;
Line 25, replace "(lap and pre-alpha" with --(IαI) and pre-alpha--.

Signed and Sealed this
Thirteenth Day of March, 2018

Andrei Iancu
*Director of the United States Patent and Trademark Office*

UNITED STATES PATENT AND TRADEMARK OFFICE
CERTIFICATE OF CORRECTION

PATENT NO. : 9,758,570 B2  
APPLICATION NO. : 14/859705  
DATED : September 12, 2017  
INVENTOR(S) : Yow-Pin Lim et al.

Page 1 of 1

It is certified that error appears in the above-identified patent and that said Letters Patent is hereby corrected as shown below:

In the Specification

Column 1, Lines 17-20, replace:
"This work was supported by National Institutes of Health/National Institute of General Medical Sciences Grants, Grant Nos. 2R44GM65667-02 and 1R43GM079071-01A1."

With:
--This invention was made with government support under Grant Numbers R44 GM065667 and R43 GM079071 awarded by the National Institutes of Health.--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*